(12) United States Patent
Chen et al.

(10) Patent No.: US 11,769,586 B2
(45) Date of Patent: Sep. 26, 2023

(54) MEDICAL CLOUD PLATFORM DATA SHARING SYSTEM AND METHOD BASED ON THIRD-PARTY BUSINESS

(71) Applicant: Shanghai SVM Medical Technology Co., Ltd., Shanghai (CN)

(72) Inventors: Yundai Chen, Shanghai (CN); Xiaobo Huang, Shanghai (CN); Baoshi Han, Shanghai (CN); Yun Long, Shanghai (CN); Yujie Zhou, Shanghai (CN); Qian Zhai, Shanghai (CN); Shiwei Yang, Shanghai (CN); Junbao Shan, Shanghai (CN); Haiqing Gao, Shanghai (CN); Weihua Lv, Shanghai (CN); Jian Sun, Shanghai (CN); Jinjing Zhang, Shanghai (CN)

(73) Assignee: Shanghai SVM Medical Technology Co., Ltd., Shanghai (CN)

( * ) Notice: Subject to any disclaimer, the term of this patent is extended or adjusted under 35 U.S.C. 154(b) by 401 days.

(21) Appl. No.: 17/052,582

(22) PCT Filed: May 15, 2019

(86) PCT No.: PCT/CN2019/087110
§ 371 (c)(1),
(2) Date: Nov. 3, 2020

(87) PCT Pub. No.: WO2019/219036
PCT Pub. Date: Nov. 21, 2019

(65) Prior Publication Data
US 2021/0074415 A1 Mar. 11, 2021

(30) Foreign Application Priority Data
May 16, 2018 (CN) .......................... 201810469182.5

(51) Int. Cl.
*G16H 40/20* (2018.01)
*G16H 40/67* (2018.01)
(Continued)

(52) U.S. Cl.
CPC ........... *G16H 40/20* (2018.01); *A61B 5/0022* (2013.01); *G06N 3/08* (2013.01); *G06Q 30/018* (2013.01);
(Continued)

(58) Field of Classification Search
CPC ........ G16H 40/20; G16H 10/60; G16H 15/00; G16H 40/40; G16H 40/67; G16H 50/20;
(Continued)

(56) References Cited

U.S. PATENT DOCUMENTS

2014/0123292 A1 5/2014 Schmidt et al.
2016/0378943 A1* 12/2016 Vallée .................... G16H 40/63
705/2
(Continued)

FOREIGN PATENT DOCUMENTS

CN 105380602 A 3/2016
CN 105608340 A 5/2016
(Continued)

OTHER PUBLICATIONS

International Search Report issued in PCT application No. PCT/CN2019/087110.
(Continued)

*Primary Examiner* — Austin J Moreau
(74) *Attorney, Agent, or Firm* — SYNCODA LLC; Feng Ma

(57) ABSTRACT

The present application relates to a system and method for sharing data on a medical cloud platform based on third-party business. The system includes: a terminal device and a cloud platform. The cloud platform receives a massive
(Continued)

quantity of vital-sign data that are sent by the terminal device, analyzes and processes the massive quantity of vital-sign data by using the deep-learning framework of distributed parallel computation, screens abnormal data, and sends an abnormal-event warning to the user, to prompt the medical care personnel to quickly intervene. The terminal device may send an instruction to the cloud platform, including a user-self-defined-term setting instruction, a real-time-data service instruction, a data invoking instruction, a medical-document service instruction, a consultation-service instruction, a medical-cooperation-information issuing instruction, a data analyzing and counting instruction, a patient-state evaluating instruction, a data-analysis-report managing instruction, and a medical-tool-library inquiring instruction, to obtain the support from various third-party-business services.

16 Claims, 11 Drawing Sheets

(51) Int. Cl.
| | |
|---|---|
| *G16H 10/60* | (2018.01) |
| *G16H 15/00* | (2018.01) |
| *G16H 50/20* | (2018.01) |
| *G16H 40/40* | (2018.01) |
| *A61B 5/00* | (2006.01) |
| *G06N 3/08* | (2023.01) |
| *G06Q 30/018* | (2023.01) |
| *H04L 9/40* | (2022.01) |
| *H04L 67/10* | (2022.01) |

(52) U.S. Cl.
CPC .............. *G16H 10/60* (2018.01); *G16H 15/00* (2018.01); *G16H 40/40* (2018.01); *G16H 40/67* (2018.01); *G16H 50/20* (2018.01); *H04L 63/08* (2013.01); *H04L 67/10* (2013.01)

(58) Field of Classification Search
CPC ........ G16H 80/00; A61B 5/0022; G06N 3/08; G06Q 30/018; H04L 63/08; H04L 67/10; H04L 67/1097; G06F 21/6245
See application file for complete search history.

(56) References Cited

U.S. PATENT DOCUMENTS

2018/0032691 A1* 2/2018 Zur ..................... A61B 5/259
2018/0256111 A1* 9/2018 Ganapathy ............ G16H 50/30

FOREIGN PATENT DOCUMENTS

| | | |
|---|---|---|
| CN | 106997421 A | 8/2017 |
| CN | 107145704 A | 9/2017 |
| CN | 108648786 A | 10/2018 |

OTHER PUBLICATIONS

Office Action issued in Chinese patent application No. 201810469182.5, dated Jun. 30, 2020.

* cited by examiner

MEDICAL CLOUD PLATFORM DATA SHARING SYSTEM AND METHOD BASED ON THIRD-PARTY BUSINESS

CROSS-REFERENCE TO RELATED APPLICATIONS

This application claims priority to Chinese Patent Application No. 201810469182.5, filed on May 16, 2018, and International Patent Application No. PCT/CN2019/087110, filed on May 15, 2019, both of which are hereby incorporated by reference in their entireties.

TECHNICAL FIELD

The present application relates to the field of medical cloud platforms, and particularly relates to a system and method for sharing data on a medical cloud platform based on third-party business.

BACKGROUND

Vital-sign monitoring devices, including bedside multi-parameter monitors, respiration-function monitors, intracranial-pressure monitors and fetal-heart monitors, are the major equipment of Intensive Care Units (ICU) of hospitals, and specialized ICUs, such as cardiology department, pneumology department, neurosurgery department, emergency department, and obstetrics and gynecology department, are used to monitor in real time the vital-sign data of patients, and are of vital importance for saving the lives of the patients. In the United States, ICUs serve to monitor millions of patients annually. China is the country that has the largest quantity of ICUs in the world, and the hospitals all over the country have currently millions of vital-sign monitoring devices of various types, the quantity of which is still quickly growing.

Globally, vital-sign monitoring devices have some problems. Each of the devices generates hundreds of MB of data every day, but the devices do not have the capacity of long-term data storage. The false-alarming rates of the devices are extremely high. The devices cannot generate electronic data analysis reports, and the medical care personnel of the ICUs in the hospitals are required to artificially in real time analyze and discriminate the data, and manually transcribe the data of the relative information. Therefore, the medical care personnel of the ICUs in the hospitals all over the world are always in the state of high load, and are utterly exhausted. In addition, small and medium-scale hospitals always lack ICU medical care personnel, and are not capable of handling the complicated and onerous processing of vital-sign data, which directly affects the quality of medical care. The ICU clinical information system (CIS), which has emerged in recent years, can reduce part of the labor intensity of ICU, but it does not solve the problem of the analysis and management of vital-sign data of the users. Moreover, the CIS requires the users to obtain the support of the Hospital Information-management System (HIS), which is very expensive. In the prior art, generally, the data of the bedside multi-parameter monitoring devices of lower-level hospitals are remotely sent to upper-level hospitals, for the upper-level hospitals to facilitate the lower-level hospitals in the analysis and diagnosis of the vital-sign data, and to instruct the clinical medical treatment. However, when a large quantity of ICU patient data from lower-level hospitals are altogether concentrated to upper-level hospitals to be processed, the upper-level hospitals will bear a huge pressure, which is insufferable, so the approach is difficult to be utilized in a large scale.

Globally, vital-sign monitoring devices have already had multiple data communication interfaces, but each of the manufacturers has his own communication protocols and data formats, which are incompatible. Some of the solutions of the prior art may solve the problem of the data receiving service of the devices of other manufacturers, but they do not solve the problem of the different data formats of the manufacturers. It is required to install multiple processing software programs, and to match the data storage formats, which has an obviously low efficiency. Moreover, the communication protocols of many manufacturers do not support the inputting of patient information, so they cannot identify different patients in the same device (the same hospital bed). In hospitals, the same one device usually serves many patients. Furthermore, in some of the solutions of the prior art, the module of the vital-sign-data source is equipped with and connected to a message processing module and a communication module, and the communication module is connected to Internet, to send the data to a cloud calculation module and a cloud-side database. Such a technique adds the intermediate processing step between each of the devices of the manufacturers and the cloud platform, whereby the complexity and the cost of each of the devices are obviously increased, and the reliability is reduced.

SUMMARY

In view of the above analysis, the present application aims at providing a system and method for sharing data on a medical cloud platform based on third-party business, to solve the problems of the analysis and processing of the massive quantity of vital-sign data of the user, and solve the problems of the onerous labor intensity and working pressure of the medical care personnel, to improve the quality of medical care and the working efficiency.

The objects of the present application are realized mainly by using the following technical solutions.

In an aspect, there is provided a system for sharing data on a medical cloud platform based on third-party business, wherein the system comprises: a terminal device and a cloud platform;

the cloud platform comprises: a cloud-platform data communication subsystem, a cloud-platform data support subsystem and a cloud-platform third-party-business subsystem;

the cloud-platform data communication subsystem is configured for data communication between the cloud-platform third-party-business subsystem and the terminal device;

the cloud-platform data support subsystem is configured to, by applying a deep-learning framework of distributed parallel computation, process and store in real time data received by the cloud-platform;

the cloud-platform third-party-business subsystem is configured to provide third-party business according to a service requesting instruction of the terminal device, and is further configured to perform auxiliary analysis and checking on abnormal data that is processed by the cloud-platform data support subsystem; and the terminal device comprises: a service terminal device and a vital-sign monitoring device, and is configured to send data to the cloud-platform according to a destination address, and receive service of the third-party business.

The advantageous effects of the present application are as follows. By using the third-party-business service, the solution solves the difficulty in the analysis, interpretation and storage of the massive quantity of vital-sign data of many hospitals, and also solves the problem of the lack of data analysis reports, which reduces the labor intensity of the medical care personnel, and improves the quality of medical care and the working efficiency.

Optionally, the data include: a service instruction and vital-sign data;

the cloud-platform data communication subsystem comprises: a data communicator and a data preprocessor;

the data communicator is configured to receive in real time data of a plurality of terminal devices, and interact data with a user, send the service instruction in the data to the cloud-platform third-party-business subsystem, and transmit the vital-sign data to the data preprocessor;

the data preprocessor is configured to bind an ID code of a vital-sign monitoring device and patient information to generate a service serial number, and simultaneously perform resolving, classification and data-format standardizing processing of the vital-sign data, reserve a device-initial-alarming-event identifier, encapsulate integrally the service serial number and the vital-sign data as preprocessed, and save the encapsulated data into a vital-sign database;

the cloud-platform third-party-business subsystem comprises a first processor of third-party-business serving and a third-party-business terminal; the first processor of third-party-business serving is configured to receive the service instructions, and provide a third-party-business service to the user; and the third-party-business terminal is configured for the auxiliary analysis and checking of the vital-sign data of the cloud platform;

the cloud-platform data support subsystem comprises: a message bus, a data storage and a second processor of real-time analyzing and processing;

the message bus is configured to connect and control data transmission among the subsystems and the processors, the message bus, the data storage, the data communicator and the data preprocessor of the cloud platform;

the data storage comprises the vital-sign database, a file database, a business-information database and a buffer database, and is configured for storing and invoking of the data; and the second processor of real-time analyzing and processing is configured to read in real time data in the vital-sign database, perform analysis and processing, generate a data analysis report, and send the data analysis report to the service terminal device for browsing and reading, and simultaneously save the data analysis report into the file database.

The advantageous effects that can be obtained by using the above optional solution are as follows. By using the format standardizing preprocessing of the vital-sign data, the solution solves the problem of non-uniform data formats of external devices, which reduces the complexity of the data processing, and improves the working efficiency of the cloud platform.

By associating the service serial number with the user information, the clinical information and the data information, and performing bidirectional mapping and conversion with the device ID, the solution solves the problem of identifying different patients in the same device (the same hospital bed), and at the same time establishes reliable and high-efficiency internal and external logical relations of data inquiring and data interaction, which satisfies the requirements on the internal data inquiring of the system and the interaction with external data.

Optionally, the second processor of real-time analyzing and processing is configured to perform real-time analysis and screening of the vital-sign data by using a mode of on-line real-time data analysis and processing and a deep-learning framework based on Spark engine;

the deep-learning framework of the Spark distributed parallel computation is configured to read in real time the vital-sign data in the vital-sign database, wherein the Spark engine is configured to, according to a preset micro-batching time interval, create in parallel a plurality of tasks, trigger a Spark Streaming to split the data by types into RDD data collections, and simultaneously control a center model of a corresponding type to calculate and process the type of data; and the center model is configured to, when abnormal data that exceed a preset reference are found by the calculating and processing, analyze features of the abnormal data, calculate a duration, and mark an attribute of the abnormal data, and the second processor of real-time analyzing and processing is configured to, according to the service serial number, send an abnormal-event warning to the user, generate a real-time-data analysis report, send the data analysis report to the service terminal device for browsing and reading, and save the data analysis report into a file database;

the second processor of real-time analyzing and processing is configured to integrate the vital-sign data of a whole process of a user that have been in real time analyzed and screened, generate a dynamic-data analysis report, send the dynamic-data analysis report to the service terminal device for browsing and reading, and save the dynamic-data analysis report into a file database; and the second processor of real-time analyzing and processing is configured to, by using the vital-sign data that have been analyzed and screened, train and optimize in real time a center model of each type, to obtain a new center model of the type of data.

The advantageous effects that can be obtained by using the above optional solution are as follows. By using the advantages of the distributed type, high throughput and self-learning of the deep-learning framework based on the Spark engine, the solution supports the cloud platform to provide to the user a massive quantity of vital-sign-data service, and the real-time auxiliary analysis and checking by a third party further guarantees the quality of the data service of the cloud platform, which has an extensive applicability.

By learning and optimizing the center model in real time by using the quantitative and qualitative data of the vital-sign database, the solution improves the accuracy of the center model, and in turn improves the efficiency of the processing of the massive quantity of vital-sign data.

By analyzing and calculating in real time the vital-sign data and the contained device-initial-alarming-event data, screening abnormal data, and sending a warning to the user, the solution improves the accuracy of the abnormal-event warning, and effectively reduces device-false-alarming events, which frequently happen in monitoring processes.

Optionally, the third-party-business terminal is connected to the cloud platform, and is configured to perform real-time auxiliary analysis and checking of the vital-sign data that have been in real time analyzed and processed, and the second processor of real-time analyzing and processing is configured to, according to a result of the auxiliary analysis, update the data in the vital-sign database, and use the data to generate the data analysis report. Optionally, the service instructions is formed by an instruction name and a parameter, and includes: a real-time-data service instruction, a data invoking instruction, a user-self-defined-term setting instruction, a consultation initiating instruction, a device-remote-operation instruction, a medical-cooperation-information issuing instruction, a medical-document service instruction, a data-analysis-report managing instruction, a data analyzing and counting instruction, a patient-state evaluating instruction and a medical-tool-library inquiring instruction.

The advantageous effects that can be obtained by using the above optional solution are as follows. By presetting the various complicated business operations and processes of the user as the service instructions formed by the instruction names and the parameters, and setting the processes of resolving and authenticating the service instructions, the user can quickly and safely send the instructions to the cloud platform via the terminal device, to obtain the support of the third-party-business service.

Optionally, the first processor of third-party-business serving comprises a real-time-data-service sub-processor; and the real-time-data-service sub-processor is configured to receive the real-time-data service instruction, resolve the instruction, authenticate a validity state of the ID code of the vital-sign monitoring device that is carried by the instruction, send a response message carrying license information to the data communicator, control the data communicator to receive the vital-sign data, transmit the vital-sign data to the data preprocessor to preprocess, generate the service serial number of the patient, encapsulate integrally with the data as preprocessed, save the encapsulated data into a vital-sign database, provide to the second processor of real-time analyzing and processing to be in real time analyzed and processed, generate the data analysis report, and send the data analysis report to the service terminal device for browsing and reading.

The advantageous effects that can be obtained by using the above optional solution are as follows. By authenticating the validity state of the ID code of the vital-sign monitoring device carried by the real-time-data service instruction, the solution controls invalid access, guarantees the safe and reliable operation of the cloud platform, solves the difficulty in the analysis and interpretation of the massive quantity of vital-sign data of the users, and solves the problem of the lack of data analysis reports, which improves the quality of medical care and the working efficiency of the user.

Optionally, the first processor of third-party-business serving comprises a data invoking sub-processor; the data invoking sub-processor is configured to receive the data invoking instruction, resolve the instruction, authenticate user information and a validity state of user privilege that are carried by the instruction, send a response message carrying license information to the service terminal device, according to the patient information and a type of the invoked data carried by the instruction, map the service serial number of the patient, perform data retrieving and invoking, and provide the invoked data to the service terminal device for browsing, reading, real-time live broadcast, and historical playback; a record of the data invoking operation is saved into the business-information database; and the types of the data include: real-time data and historical data.

The advantageous effects that can be obtained by using the above optional solution are as follows. The solution provides a convenient data invoking tool to the user, by supporting the user to quickly acquire accurate and complete data information, know the variation of the illness of the patient, evaluate the medical effect, and prepare the medical decision making solution, which improves the quality of medical care and the working efficiency. Moreover, the solution saves the record of the data invoking operation, which guarantees the data safety of the cloud platform and the user.

Optionally, the first processor of third-party-business serving comprises a medical-document managing sub-processor; the medical-document managing sub-processor is configured to receive the medical-document service instruction, resolve the instruction, authenticate user information and a validity state of user privilege that are carried by the instruction, send a response message carrying license information to the service terminal device, according to the patient information and information of a type of the medical document carried by the instruction, map the service serial number of the patient, retrieve the medical document that meets the instruction parameters, and provide the medical document to the service terminal device, and the service terminal device performs managing operations of creating, editing, inquiring, maintaining and storing by handwriting, voice or spelling; a record of the managing operations is saved into the business-information database; and the information of the types of the medical document includes: a long-term medical advice, a temporary medical advice, a nursing form and an electronic case history.

The advantageous effects that can be obtained by using the above optional solution are as follows. The solution provides a convenient tool of electronization of medical documents to the user, by converting the tedious handwriting transcription or keyboard entering of various medical documents of the user into the handwriting, voice or spelling inputting at the terminal device, which reduces the operation complexity for the medical care personnel, and improves the efficiency of the medical service. Moreover, the solution saves the record of the managing operations, which guarantees the reliability, safety and traceability of the medical documents.

Optionally, the first processor of third-party-business serving comprises a user-self-defined-term setting sub-processor; the user-self-defined-term setting sub-processor is configured to receive the user-self-defined-term setting instruction, resolve the instruction, authenticate user information and a validity state of user privilege that are carried by the instruction, send a response message carrying license information to the service terminal device, and permit the user to edit, update and store the user-self-defined term, and the cloud platform executes the setting as updated; a record of the user-self-defining setting operation is saved into the business-information database; and the user-self-defined term includes: a threshold of abnormity of the vital-sign data, a rule configuration of system and service, a mode and range of message notification, options of items of third-party businesses, and setting of a user operation interface.

The advantageous effects that can be obtained by using the above optional solution are as follows. The solution provides a convenient tool of setting the user-self-defined terms to the user, by supporting the user to, according to the illness, set the thresholds of abnormity in a personalized manner, and set the rule configuration of system and service, the mode and range of message notification, the options of items of third-party businesses, and the user operation interface, which improves the working efficiency of the user. Moreover, the solution saves the record of the setting operation, which guarantees the safety of the cloud platform and the user system.

Optionally, the first processor of third-party-business serving comprises a device-remote-operation-service sub-processor; the device-remote-operation-service sub-processor is configured to receive the device-remote-operation instruction, resolve the instruction, authenticate user information and a validity state of user privilege that are carried by the instruction, and send a response message carrying license information to the service terminal device, and simultaneously, according to information of one or more patients carried by the instruction, map IDs of one or more vital-sign monitoring devices, and retrieve and connect to devices that meet the instruction parameters, and the service terminal device performs operations of control measurement, state inquiring, configuration modification and equipment maintenance; the acquired operation result is saved into a corresponding database according to the data type; and a record of the device remote operation is saved into the business-information database.

The advantageous effects that can be obtained by using the above optional solution are as follows. The solution provides a convenient tool of device remote operation to the user, by supporting the user-service terminal device to remotely control the vital-sign monitoring device, and change/adjust the working mode of the device, which satisfies the demands of the user. Moreover, the solution saves the record of the device remote operation, which guarantees the safety of the cloud platform and the user system.

Optionally, the first processor of third-party-business serving comprises a consultation-service sub-processor; the consultation-service sub-processor is configured to receive the consultation initiating instruction, resolve the instruction, authenticate user information and a validity state of user privilege that are carried by the instruction, and send a response message carrying license information to the service terminal device, and simultaneously, according to patient information and consultation-party information carried by the instruction, send to a consultation party via the cloud platform a notification of starting a terminal-device consultation, establish a data link between an initiating party and the consultation party, according to the patient information, map the service serial number, share patient data, and perform multi-media video consultation and data information interaction; file data of the consultation information are saved into the file database; a record of the consultation operation is saved into the business-information database; and the patient data include: vital-sign data, clinical information, a data-analysis-report file, an image-video file, and a medical-document file.

The advantageous effects that can be obtained by using the above optional solution are as follows. The solution provides a convenient tool of consultation to small and medium-scale hospitals, by establishing on the cloud platform the sharing of the medical data and the medical resource between them and large-scale hospitals, to realize the data sharing and consultation for high-risk intractable cases, and instruct the clinical medical treatment of the small and medium-scale hospitals, which improves the medical level of the small and medium-scale hospitals and the utilization of the medical resource of the whole society.

Optionally, the first processor of third-party-business serving comprises a medical-cooperation-information issuing sub-processor; the medical-cooperation-information issuing sub-processor is configured to receive the medical-cooperation-information issuing instruction, resolve the instruction, authenticate user information and a validity state of user privilege that are carried by the instruction, and send a response message carrying license information to the service terminal device, and simultaneously, according to patient information and information of a medical cooperation team that are carried by the instruction, issue cooperation information via the cloud platform to a terminal device of the medical cooperation team, and prompt by using acousto-optic effect, vibration or image-text; and a record of the medical-cooperation-information issuing operation is saved into the business-information database.

The advantageous effects that can be obtained by using the above optional solution are as follows. The solution supports the user to establish a multi-discipline medical cooperation mechanism, and can extend the multi-discipline medical cooperation mechanism beyond the user, to quickly and effectively concentrate the medical resource of the user, to provide service to patients of emergency treatment and high-risk intractable patients, which improves the quality of medical care and the working efficiency.

In another aspect, there is further provided a method for sharing data on a medical cloud platform based on third-party business, wherein the method comprises the steps of:

by a terminal device that has passed identity authentication, sending data to the cloud-platform according to a destination address;

by a data communicator, receiving in real time data of a plurality of terminal devices, wherein the data include: a service instruction and vital-sign data, sending the service instruction to a first processor of third-party-business serving, and transmitting the vital-sign data to the data preprocessor;

by the first processor of third-party-business serving, receiving the service instruction, and according to parameters carried by the service instruction, providing a third-party-business service to the user;

by the data preprocessor, based on a system coding-schedule regulation, binding an ID code of a vital-sign monitoring device and patient information to generate a service serial number;

performing resolving, classification and data-format standardizing processing of the acquired vital-sign data of each of users, and reserving a device-initial-alarming-event identifier;

encapsulating integrally the service serial number of the patient and the data as preprocessed, and saving the encapsulated data into a vital-sign database; and by a second processor of real-time analyzing and processing, reading in real time the vital-sign data, performing analysis and processing, and generating a data analysis report.

The advantageous effects that can be obtained by using the above method are as follows. By using the third-party-business service, the solution solves the difficulty in the analysis, interpretation and storage of the massive quantity of vital-sign data of the users, and also solves the problem of the lack of data analysis reports, which improves the quality of medical care and the working efficiency.

By using the format standardizing processing of the vital-sign data, the solution solves the problem of non-uniform data formats of external devices, which reduces the difficulty in the data processing, and improves the working efficiency of the cloud platform.

By associating the service serial number with the user information, the clinical information and the data information, and performing bidirectional mapping and conversion with the device ID, the solution solves the problem of addressing and identifying of data inquiring and data interaction of the cloud platform, solves the problem of identifying different patients in the same device (the same hospital bed), and at the same time establishes reliable and high-efficiency internal and external logical relations of data inquiring and data interaction, which satisfies the requirements on the internal data inquiring of the system and the interaction with external data.

Optionally, the third-party-business service includes a real-time-data service, and a process of the real-time-data service comprises the steps of:

by the service terminal device, inputting patient information and an ID code of the vital-sign monitoring device, and sending a real-time-data service instruction to the cloud platform;

by the data communicator, sending the received instruction to a real-time-data-service sub-processor;

by the real-time-data-service sub-processor, receiving the instruction, resolving the instruction, authenticating a validity state of the ID code of the vital-sign monitoring device that is carried by the instruction, sending a response message carrying license information to the data communicator, permitting to receive the vital-sign data, and transmitting to the data preprocessor;

by the data preprocessor, performing preprocessing to the vital-sign data, generating a service serial number, encapsulating integrally the service serial number and the vital-sign data as preprocessed, and saving the encapsulated data into a vital-sign database;

by the second processor of real-time analyzing and processing, reading in real time the vital-sign data in the vital-sign database by using a mode of on-line real-time data analysis and processing and a deep-learning framework based on Spark engine;

wherein the Spark engine is configured to, according to a preset micro-batching time interval, create in parallel a plurality of tasks, and trigger a Spark Streaming to split the data by types into RDD data collections, and simultaneously control a center model of a corresponding type to calculate and process the type of data;

by the center model, finding abnormal data that exceed a preset reference, analyzing features of the abnormal data, calculating a duration, and marking an attribute of the abnormal data;

by the second processor of real-time analyzing and processing, generating a real-time-data analysis report according to the abnormal data, sending an abnormal-event warning to the user, sending the analysis report to the service terminal device, and saving the analysis report into a file database;

by the second processor of real-time analyzing and processing, integrating the vital-sign data of a whole process of a user that have been analyzed and screened, generating a dynamic-data analysis report, sending the dynamic-data analysis report to the service terminal device, and saving the dynamic-data analysis report into a file database; and by a third-party-business terminal, performing real-time auxiliary analysis and checking to the vital-sign data that have been analyzed and processed, and by the second processor of real-time analyzing and processing, according to a result of the auxiliary analysis, updating the data in the vital-sign database, and using the data to generate the data analysis report.

The advantageous effects that can be obtained by using the above optional solution are as follows. By authenticating the validity state of the ID code of the vital-sign monitoring device carried by the real-time-data service instruction, the solution controls invalid access, guarantees the safe and reliable operation of the cloud platform, solves the difficulty in the analysis and interpretation of the massive quantity of vital-sign data of the users, and solves the problem of the lack of data analysis reports. The auxiliary analysis and checking by a third party further guarantees the quality of the data service of the cloud platform, which improves the quality of medical care and the working efficiency, and reduces the labor intensity and the working pressure of the medical care personnel.

By using the advantages of the distributed type, high throughput and self-learning of the deep-learning framework based on the Spark engine, the solution supports the cloud platform to provide to the user a massive quantity of vital-sign-data service, and the auxiliary analysis and checking by a third party guarantees the quality of the data service, which has an extensive applicability. The solution learns, trains and optimizes in real time the center model, which improves the accuracy of the center model, and in turn improves the efficiency of the processing of the massive quantity of vital-sign data.

Optionally, the third-party-business service further includes a data invoking service, and a process of the data invoking service comprises the steps of:

by the service terminal device, inputting patient information and information of type of invoked data, and sending a data-invoking-service instruction to the cloud platform;

by the data communicator, sending the received instruction to a data-invoking-service sub-processor;

by the data-invoking-service sub-processor, receiving the instruction, resolving the instruction, authenticating user information and a validity state of user privilege that are carried by the instruction, and sending a response message carrying license information to the user-service terminal device;

by the data-invoking-service sub-processor, according to the patient information carried by the instruction, retrieving the mapped service serial number;

by the data-invoking-service sub-processor, according to the service serial number, retrieving and invoking data that meet the instruction parameters;

by the data-invoking-service sub-processor, providing the invoked data to the user-service terminal device for browsing, reading, real-time live broadcast, and historical playback; and by the data-invoking-service sub-processor, saving a record of the data-invoking-service operation into a business-information database.

The advantageous effects that can be obtained by using the above optional solution are as follows. The solution provides a convenient data invoking tool to the user, by supporting the user to quickly acquire accurate and complete data information, know the variation of the illness of the patient, evaluate the medical effect, and prepare the medical decision making solution, which improves the quality of medical care and the working efficiency. Moreover, the solution saves the record of the data invoking operation, which guarantees the data safety of the cloud platform and the user.

Optionally, the third-party-business service further includes a medical-document managing service, and a process of the medical-document managing service comprises the steps of:

by the service terminal device, inputting patient information and information of type of a medical document, and sending a medical-document service instruction to the cloud platform;

by the data communicator, sending the received instruction to a medical-document managing sub-processor;

by the medical-document managing sub-processor, receiving the instruction, resolving the instruction, authenticating user information and a validity state of user privilege that are carried by the instruction, and sending a response message carrying license information to the user-service terminal device;

by the medical-document managing sub-processor, according to the patient information carried by the instruction, retrieving the service serial number mapped by the patient information;

when the service serial number has been retrieved, by the medical-document managing sub-processor, according to the service serial number and the information of the type of the medical document, retrieving the medical-document file that meets the instruction parameters;

by the service terminal device, performing creating, editing, inquiring, and maintaining of the selected medical-document file by handwriting, voice or spelling inputting, and saving the medical-document file that has been processed into the file database;

when the retrieving result of the service serial number is void, by the medical-document managing sub-processor, according to the patient information, creating a medical document that meets the instruction parameters, editing the medical document, and saving the medical-document file that has been processed and the patient information into the file database; and by the medical-document managing sub-processor, saving a record of the medical-document managing operation into a business-information database.

The advantageous effects that can be obtained by using the above optional solution are as follows. The solution provides a convenient tool of electronization of medical documents to the user, by converting the tedious handwriting transcription or keyboard entering of various medical documents of the user, such as a long-term medical advice, a temporary medical advice, a nursing form, an electronic case history and so on, into the handwriting, voice or spelling inputting at the terminal device, which reduces the operation complexity for the medical care personnel, and improves the efficiency of the medical service. Moreover, the solution saves the record of the managing operations, which guarantees the reliability, safety and traceability of the medical documents.

Optionally, the third-party-business service further includes a user-self-defined-term setting service, and a process of the user-self-defined-term setting service comprises the steps of:

by the service terminal device, selecting a user-self-defined term, inputting a setting content, and sending a user-self-defined-term setting instruction to the cloud platform;

by the data communicator, sending the received instruction to a user-self-defined-term setting sub-processor;

by the user-self-defined-term setting sub-processor, receiving the instruction, resolving the instruction, authenticating user information and a validity state of user privilege that are carried by the instruction, and sending a response message carrying license information to the user-service terminal device;

by the user-service terminal device, performing setting operations of editing, updating and storing to the user-self-defined term, and by the cloud platform, executing the setting as updated; and by the user-self-defined-term setting sub-processor, saving a record of the setting operation into a business-information database.

The advantageous effects that can be obtained by using the above optional solution are as follows. The solution provides a convenient tool of setting the user-self-defined terms to the user, wherein the user can flexibly perform the setting according to the working requirements and the working habits, including setting the thresholds of abnormal data in a personalized manner according to the illness of the patient. Moreover, the solution saves the record of the setting operation, which guarantees the safety of the cloud platform and the user system.

Optionally, the third-party-business service further includes a device-remote-operation service, and a process of the device-remote-operation service comprises the steps of:

by the service terminal device, inputting information of one or more patients and information of type of a remote operation, and sending a device-remote-operation instruction to the cloud platform;

by the data communicator, sending the received instruction to a device-remote-operation sub-processor.

by the device-remote-operation submodule, receiving the instruction, resolving the instruction, authenticating user information and a validity state of user privilege that are carried by the instruction, and sending a response message carrying license information to the user-service terminal device;

by the device-remote-operation sub-processor, according to IDs of one or more vital-sign monitoring devices mapped by the patient information, retrieving the device that meets the instruction parameters, and establishing a connection;

by the service terminal device, performing operations of control measurement, state inquiring, configuration modification and equipment maintenance of the connected vital-sign monitoring devices; and by the service terminal device, completing the connection and operation, and by the device-remote-operation sub-processor, saving the acquired operation result into a corresponding database according to the data type; and saving a record of the device remote operation into a business-information database.

The advantageous effects that can be obtained by using the above optional solution are as follows. The solution provides a convenient tool of device remote operation to the user, by supporting the user-service terminal device to remotely control the vital-sign monitoring device, and change/adjust the working mode of the device, which satisfies the application demands of the user, and improves the working efficiency. Moreover, the solution saves the record of the device remote operation, which guarantees the safety of the cloud platform and the user system.

In the present application, the above technical solutions may be combined, to implement more preferable combined solutions. The other characteristics and advantages of the present application will be described in the subsequent description, and part of the advantages can become apparent from the description or be understood by the implementation of the present application. The objects and the other advantages of the present application can be implemented and obtained from the contents particularly illustrated in the description, the claims and the drawings.

BRIEF DESCRIPTION OF THE DRAWINGS

The drawings are merely for the purpose of illustrating the particular embodiments, and are not considered as limitation to the present application. Throughout the drawings, the same reference signs denote the same elements.

DESCRIPTION OF EMBODIMENTS

Figure 1:
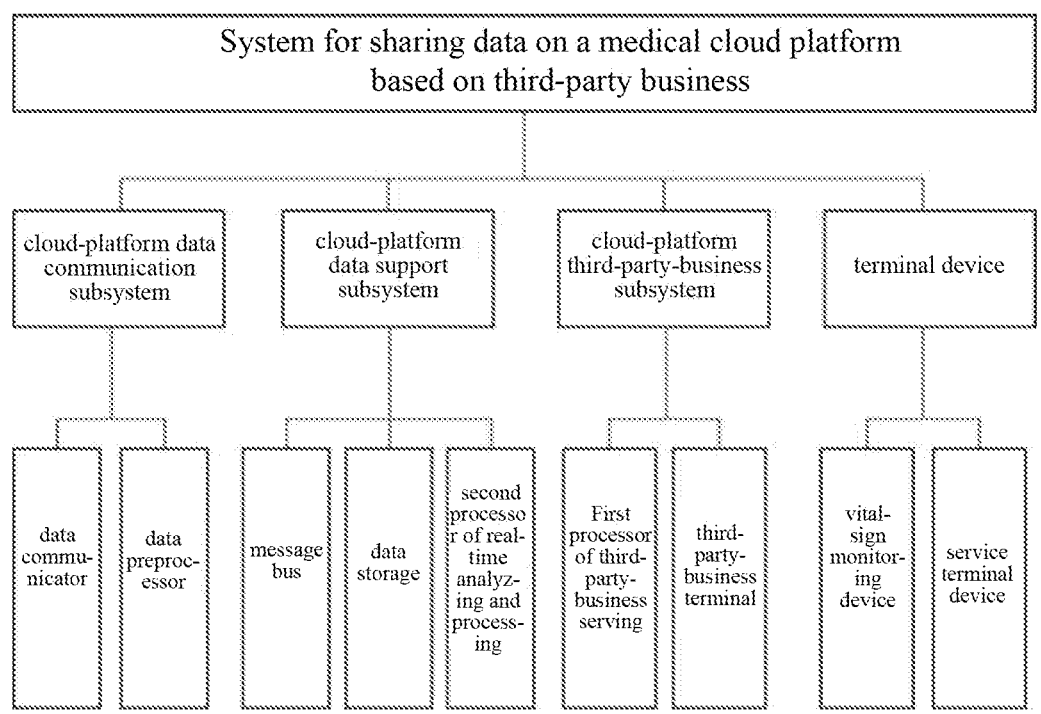
FIG. 1 is a block diagram of the system for sharing data on a medical cloud platform based on third-party business according to an embodiment of the present application.

The preferable embodiments of the present application will be particularly described below by referring to the drawings. The drawings form part of the present application, are used to explain the principle of the present application together with the embodiments of the present application, and are not limiting the scope of the present application.

A particular embodiment of the present application discloses a system for sharing data on a medical cloud platform based on third-party business. As shown in FIG. 1, the system comprises: a terminal device and a cloud platform;

the cloud platform comprises: a cloud-platform data communication subsystem, a cloud-platform data support subsystem and a cloud-platform third-party-business subsystem;

the cloud-platform data communication subsystem is configured for data communication between the cloud-platform third-party-business subsystem and the terminal device;

the cloud-platform data support subsystem is configured to, by applying a deep-learning framework of distributed parallel computation, process and store in real time data received by the cloud-platform;

the cloud-platform third-party-business subsystem is configured to provide third-party business according to a service requesting instruction of the terminal device, and is further configured to perform auxiliary analysis and checking on abnormal data that are processed by the cloud-platform data support subsystem; and the terminal device comprises: a service terminal device and a vital-sign monitoring device, and is configured to send data to the cloud-platform according to a destination address, and receive service of the third-party business.

The cloud-platform data communication subsystem comprises: a data communicator and a data preprocessor. The data communicator is configured to connect various terminal devices, and receive in real time data of a plurality of terminal devices, and is configured for data interaction.

The data preprocessing module is configured to bind an ID code of a vital-sign monitoring device and patient information to generate a service serial number, and simultaneously perform resolving, classification and data-format standardizing processing of the vital-sign data, reserve a device-initial-alarming-event identifier, encapsulate integrally the service serial number and the data as preprocessed, and save encapsulated data into a vital-sign database.

The cloud-platform third-party-business subsystem comprises: a third-party-business serving module and a third-party-business terminal; the third-party-business serving module is configured to receive the service instruction, and provide a third-party-business service to the user; and the third-party-business terminal is configured for the auxiliary analysis and processing of the data of the cloud platform.

The cloud-platform data support subsystem comprises: a message bus, a data storage and a second processor of real-time analyzing and processing;

the message bus is configured to connect and control the transmission of data and instructions among the subsystems and the processors, the message bus, the data storage, the data communicator and the data preprocessor;

the data storage comprises the vital-sign database, a file database, a business-information database and a buffer database, and is configured for data storage and invoking; and the second processor of real-time analyzing and processing is configured to read in real time data in the vital-sign database, perform analysis and processing of it, and generate a data analysis report.

In the implementation, the cloud platform is connected to the vital-sign monitoring device (exemplarily, the vital-sign monitoring terminal device may be a multiple-parameter monitoring device, a respiration-function monitoring device, an intracranial-pressure monitoring device, and a fetal-heart-rate monitoring device), the service terminal device and the third-party-business terminal, to perform data interaction; the service terminal device, according to the destination address, sends a real-time-data service instruction to the cloud platform, the first processor of third-party-business serving resolves the instruction, authenticates a validity state of the ID code of the vital-sign monitoring device that is carried by the instruction, sends a response message carrying license information to the data communicator, and permits to receive the vital-sign data, and the data communicator establishes a connection according to a type of communication protocol, receives the data, and transmits to the data preprocessor; the data preprocessor binds the ID code of the vital-sign monitoring terminal device and the patient information in it to generate a service serial number, and simultaneously performs resolving, classification and data-format standardizing processing of the vital-sign data, reserves a device-initial-alarming-event identifier, encapsulates integrally the service serial number and the data as preprocessed, and saves the encapsulated data into a vital-sign database, the second processor of real-time analyzing and processing reads in real time the data in the vital-sign database and the contained device-initial-alarming-event data, analyzes, calculates and screens abnormal vital-sign data that exceed a preset reference, generates the data analysis report, and sends the data analysis report to the user terminal device, and the user may read, browse, download and print the report, as the basis of clinical medical treatment. The cloud platform, by business flow control and data dispatching, performs data interaction with the third-party-business terminal, the third-party-business terminal performs auxiliary analysis and checking to the data that have been analyzed and screened, and the second processor of real-time analyzing and processing, according to the result of the auxiliary analysis and checking, updates the patient data in the vital-sign database, and generates the data analysis report; and the user may send a service instruction to the cloud platform, to obtain the support from various third-party-business services.

As compared with the prior art, the cloud platform can connect to various different terminal devices of the users via a network, analyze in real time a massive quantity of vital-sign data, screen abnormal data, and generate the data analysis report, which effectively reduces device-false-alarming events, which frequently happen in the process of vital-sign monitoring, improves the quality of medical care and the working efficiency, and reduces the labor intensity of the medical care personnel. The auxiliary analysis and checking by a third party guarantees the quality of the data analysis of the cloud platform. The user terminal device can send an instruction to the cloud platform, to obtain the support from various third-party-business services, which has an extensive applicability.

It should be noted that the service terminal device and the third-party-business terminal, which are connected to the cloud platform, include at least one of a computer device, an interactive touch-screen device, a hand-held mobile device and a multi-media device, and the cloud platform may also be connected to a Hospital Information-management System (HIS), an intensive-care-unit Clinical Information System (CIS), and an Application Programming Interface (API) of a physical examination organization, a health control organization or an insurance organization.

Particularly, the data communicator has built-in communication protocols, and is configured to be connected to various different terminal devices and external systems, receive in real time the uploaded data, send the service instruction in the data to the first processor of third-party-business serving, and transmit the vital-sign data to the data preprocessor.

The data preprocessor contains a system coding schedule, and is configured to preprocess the acquired data of each of the users, generate the service serial number of the patient, encapsulate integrally the service serial number and the data as preprocessed, and save the encapsulated data into a vital-sign database, and the second processor of real-time analyzing and processing reads in real time data in the vital-sign database, and performs analyzing, screening and processing. Particularly, the process comprises:

based on a system coding-schedule regulation, binding the acquired ID code of the vital-sign monitoring terminal device and the patient information, and generating the service serial number of the patient;

performing resolving, classification and data-format standardizing processing to the received vital-sign data, and reserving the identifier of device-initial-alarming-event data; and encapsulating integrally the service serial number of the patient and the vital-sign data as preprocessed, and saving the encapsulated data into a vital-sign database.

In order to solve the problem of the incompatibility of the data formats and the communication protocols of the devices of different manufacturers, and solve the problem of identifying different patients in the same vital-sign monitoring device (the same hospital bed), the data communicator supports multiple communication protocols, including, for example, TCP/IP protocol, instant messaging protocol, HL7 protocol, DICOM protocol, multi-media communication protocol, and equipment manufacturer communication protocol. The data communicator is configured to automatically identify the user identity and the ID code of the terminal device, establish a network connection, and receive the data. The data preprocessor is configured to, based on a system coding-schedule regulation, control to bind the ID code of the vital-sign monitoring terminal device in the data and the patient information, and generate a service serial number (wherein the code of the service serial number contains time stamp, patient information, user information, device information and quantity counter), and simultaneously perform resolving, classification and data-format standardizing processing of the vital-sign data, encapsulate integrally the service serial number of the patient and the data as preprocessed, and provide to the cloud-platform system for storing, reading, invoking, analyzing and calculating.

It should be noted that the data communication subsystem of the cloud platform supports multiple communication protocols, and the data-format standardizing processing, and the service serial number and the ID of the vital-sign monitoring device may maintain bidirectional mapping and conversion, for the addressing and identifying of data inquiring and data interaction, thereby establishing flexible and high-efficiency data communication interfaces for the cloud-platform system, and the identifiers of the patient and the data, which satisfies the demands of the users on the access and data interaction of vital-sign monitoring devices and external systems of various different manufacturers, and extends the business scope and the service contents.

The message bus of the present embodiment employs message queue communication protocol, including message service and message queue interfaces, and is configured for the cloud-platform system to connect and control the business message notification and the business data transmission between the subsystems and the processors, the message bus, the data storage, the data communicator and the data preprocessor. The message queue, by business decoupling, message broadcasting and peak shifting flow control, supports the bus to transmit in real time a great quantity of messages of the system, and the reliable delivery of the message transmission, which improves the operation efficiency of the cloud-platform system.

The vital-sign database employs a structured data service system, and is configured to store the vital-sign data that have been resolved, classified and data-format standardizing processed, support high-concurrency real-time inquiries, and provide the capacities of massive storage and real-time inquiry, wherein the vital-sign data include waveform-type data and numerical-value-type data.

The file database employs an object storage service system, and is configured to store various files generated by the business system, and upload the data files to the storage space in the form of objects, wherein the files include unstructured data files such as files of patient information, files of clinical information, files of vital-sign-data reports, files of medical documents, files of multi-media video, files of medical reference books and so on.

The business-information database employs a database of relational-model-organization data, and is configured for the cloud platform to store structured business data, and control the inquiring and storage of the data of the business logical relations between the processors, which has the advantage of maintaining the data consistency.

The buffer database employs a non-relational database, and is configured to control the data exchange between the processors and the state maintaining, and also configured to buffer the results of database inquiring, which reduces the times of the accessing the database, and increases the response speed of the cloud platform.

It should be noted that the data storage of the present embodiment integrates the advantages of the various databases and data storage service systems, solves the problem of managing large-scale data collections, diverse data structures and diverse data categories by the cloud platform, and supports the operation of the cloud platform in high-concurrency environments.

Figure 3:
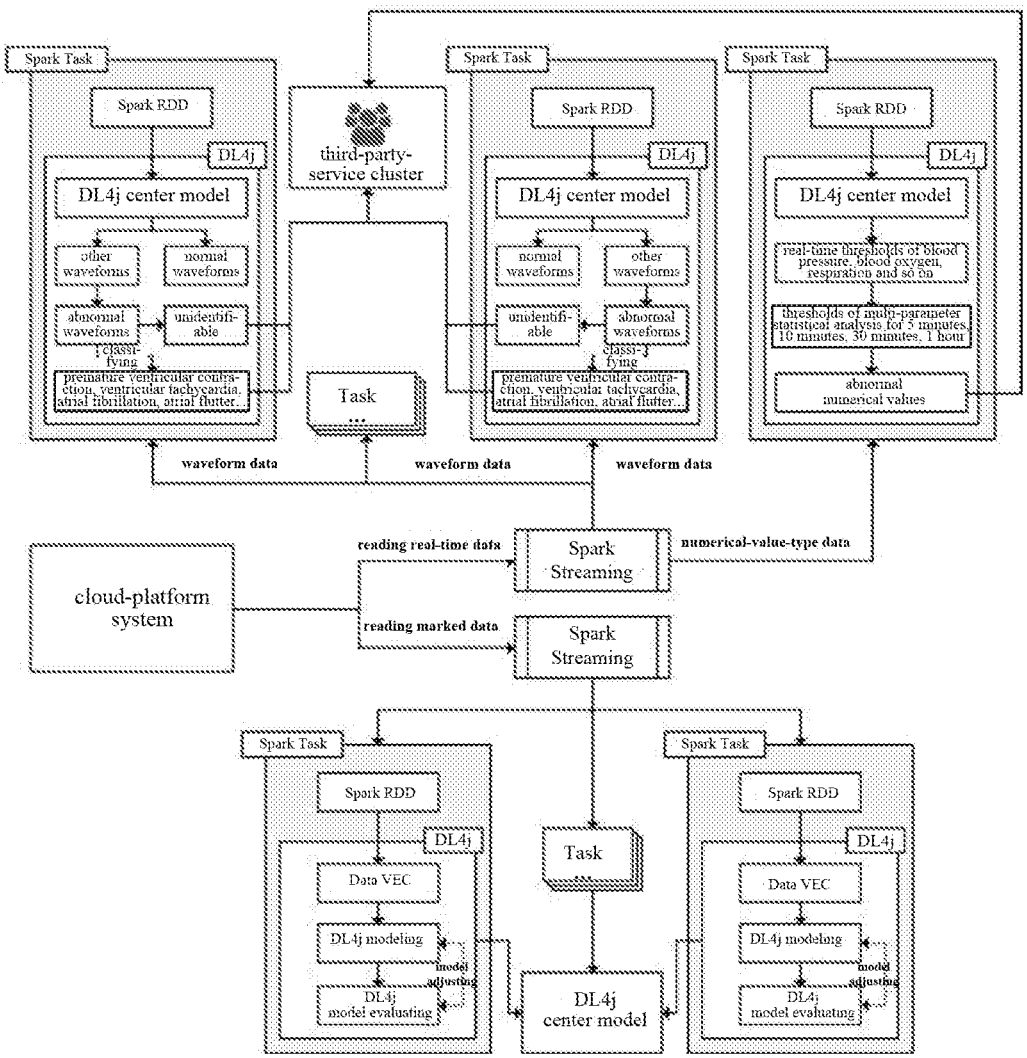
FIG. 3 is a diagram of deep-learning framework based on Spark distributed parallel computation according to an embodiment of the present application.

The second processor of real-time analyzing and processing is configured for processing in real time the vital-sign data. As shown in FIG. 3, the present embodiment employs the deep-learning framework of the Spark distributed parallel computation to read in real time the vital-sign data in the vital-sign database and the contained device-initial-alarming data, wherein the Spark engine is configured to, according to a preset micro-batching time interval, create in parallel a plurality of tasks, and trigger a Spark Streaming to split the data by types into RDD data collections, and simultaneously control a center model of a corresponding type to calculate and process the type of data; and the process comprises the steps of: by the center model, when abnormal data that exceed a preset reference are found by the calculating and processing, analyzing features of the abnormal data, calculating a duration, and marking an attribute of the abnormal data;

by the second processor of real-time analyzing and processing, generating a real-time-data analysis report from the abnormal data, and sending an abnormal-event warning to the user;

by the second processor of real-time analyzing and processing, integrating the vital-sign data of a whole process of a user that have been analyzed and screened, outputting the vital-sign data, and generating a dynamic-data analysis report;

by the second processor of real-time analyzing and processing, saving the real-time-data analysis report and the dynamic-data analysis report into the file database; and by the second processor of real-time analyzing and processing, by using the quantitative and qualitative vital-sign data that have been analyzed and screened in the vital-sign database, learning, training and optimizing in real time a center model of each type, to obtain a new center model of the type of data.

In the above steps, the third-party-business terminal performs real-time auxiliary analysis and checking to the vital-sign data that have been processed, and the second processor of real-time analyzing and processing, according to a result of the auxiliary analysis, updates the data in the vital-sign database, and uses the data to generate the data analysis report.

It should be emphasized that the second processor of real-time analyzing and processing employs the deep-learning framework based on distributed parallel computation, which may be one of the universal frames of Spark, Storm, Flink and Samza. The deep-learning framework based on distributed parallel computation has the advantages of real-time calculation of stream data, high throughput and self-learning, greatly improves the real-time processing speed of the massive quantity of vital-sign data, effectively reduces false-alarming events, which frequently happen in the process of vital-sign monitoring, and reduces the labor intensity and the working pressure of the medical care personnel.

The center model includes two types of center models, wherein one type analyzes and calculates the patterns, rhythms and speeds of waveform-type data, and the other type analyzes and calculates the amplitudes of numerical-value-type data. The center model comprises a built-in second-order-difference calculating tool and logic analyzing tool, and is configured to calculate and analyze in real time the patterns, rhythms, speeds and numerical values of the vital-sign data, classify and mark the waveforms, count and summarize the numerical values, and screen abnormal data that exceed a reference. In order to improve the efficiency and accuracy of the analyzing and screening of the center model, the method further comprises, by using the quantitative and qualitative vital-sign data in the vital-sign database, learning, training and optimizing in real time the center model of each type, to obtain a new center model of the type of data.

It should be noted that the vital-sign data that are analyzed and processed in the present embodiment include the data of electrocatdiogram, respiration, non-invasive blood pressure, invasive blood pressure, oxyhemoglobin saturation, body temperature, pulse rate, intracranial pressure, end-tidal carbon dioxide and fetal heart rate; the waveform-type vital-sign data include: overall cardiac activity of whole process, electrocardiogram interval, QRS time limit, ST-segment evaluation pattern, QT interval, total respiration number of whole process, respiratory-wave interval, peak and trough values of pulse volume, peak and trough values of intracranial pressure, peak and trough values of partial pressure of end-tidal carbon dioxide and wave interval of partial pressure of end-tidal carbon dioxide; and the numerical-value-type vital-sign data include: systolic pressure and diastolic pressure in non-invasive/invasive blood pressure, pulse rate, oxyhemoglobin saturation, body temperature and fetal heart rate of whole process; stroke volume, cardiac index and total value of peripheral resistance of non-invasive heart stroke; and value of airway pressure, value of airway flow rate and value of airway volume of respiratory mechanics.

The features of abnormal data include: tachycardia, bradycardia, flutter-fibrillation, frequent premature beat, cardiac arrest, RonT, QT interval extension, ST-segment rising/descending, apnea, bradypnea, tachypnoea, rising/descending of oxyhemoglobin saturation, rising/descending of systolic pressure and diastolic pressure, rising/descending of mean arterial pressure, rising/descending of peak value of pulse volume, rising/descending of peak value of intracranial pressure, rising/descending of peak value of partial pressure of end-tidal carbon dioxide, rising/descending of fetal heart rate, descending of non-invasive heart stroke, and rising/descending of values of respiratory mechanics.

The center model, when abnormal data that exceed a preset reference are found by the analysis and processing, analyzes features of the abnormal data, calculates a duration of an abnormal event, and marks an attribute of the abnormal data, and simultaneously, the second processor of real-time analyzing and processing generates a real-time-data analysis report from the abnormal data, stores the real-time-data analysis report, and according to the device ID mapped by the service serial number of the patient, sends an abnormal-event warning to the user, and simultaneously sends the real-time-data analysis report to the user. It should be noted that the above preset references employ the internationally commonly used diagnostic criteria of vital-sign data as the references of the analysis and calculation.

The contents of the dynamic-data analysis report that is generated by the second processor of real-time analyzing and processing of the present embodiment include: for the whole process, comprehensive analysis and calculation, classification and marking of waveforms and oscillograms of data of dynamic electrocatdiogram, data of dynamic blood pressure, data of respiration, data of oxyhemoglobin saturation, data of invasive blood pressure, data of intracranial pressure, data of partial pressure of end-tidal carbon dioxide, data of body temperature, data of fetal heart rate, data of non-invasive heart stroke, and data of respiratory mechanics, and their tendency charts, histograms, scatter plots, and diagrams of variability analysis.

The contents of the generated real-time-data analysis report include: real-time analysis and calculation, classification and marking of waveforms, and abnormal oscillograms of data of abnormal electrocatdiogram, data of abnormal blood pressure, data of abnormal respiration, data of abnormal oxyhemoglobin saturation, data of abnormal intracranial pressure, data of abnormal partial pressure of end-tidal carbon dioxide, data of abnormal body temperature, data of abnormal fetal heart rate, data of abnormal non-invasive heart stroke, and data of abnormal respiratory mechanics, and their tendency charts.

The cloud platform saves the above data analysis reports into the file database, and the user may send a data invoking instruction to the cloud platform, to perform retrieving, inquiring, statistical analysis, reviewing and summarizing.

In order to solve the working pressure of the complicated and onerous vital-sign monitoring of the users (including hospitals, medical care personnel, patients, other facilities and so on), the users, on the basis that the corresponding privileges have been acquired, send a service instruction to the cloud platform, and the first processor of third-party-business serving resolves and authenticates the received service instruction, and, according to parameters carried by the service instruction, provides a third-party-business service to the user.

The service instruction is formed by an instruction name and a parameter, and particularly includes: a real-time-data service instruction, a data invoking instruction, an abnormal-data-event inquiring instruction, a data-analysis-report managing instruction, a medical-document service instruction, a data analyzing and counting instruction, a user-self-defined-term setting instruction, a consultation initiating instruction, a patient-state evaluating instruction, a device-remote-operation instruction, a medical-cooperation-information issuing instruction, and a medical-tool-library inquiring instruction. It should be noted that the service-instruction parameters are formed by user information, user privileges and instruction contents. The user sends a service instruction to the cloud platform via the terminal device, the data communicator sends the received service instruction to the first processor of third-party-business serving for resolving and authenticating, and the first processor of third-party-business serving provides the third-party-business service to the user according to the service-instruction parameters. The first processor of third-party-business serving includes: a real-time-data-service sub-processor, a data invoking sub-processor, a medical-document managing sub-processor, a user-self-defined-term setting sub-processor, a consultation-service sub-processor, a device-remote-operation sub-processor, a medical-cooperation-information issuing sub-processor, a patient-state evaluating sub-processor, a data-analysis-report managing sub-processor, a data analyzing and counting sub-processor and a medical-tool-library-service sub-processor.

The present embodiment divides and integrates the processes and contents of the diverse and complicated businesses of the user in a modular manner, and migrates them to the cloud platform for automated implementation, and the user obtains multiple stable and high-efficiency third-party-business services, which reduces the labor intensity and the working pressure of the medical care personnel.

Exemplarily, the real-time-data-service sub-processor is configured to, by the cloud platform, receive the real-time-data service instruction, resolve the instruction, authenticate a validity state of the ID code of the vital-sign monitoring device that is carried by the instruction, control the data communicator to receive the vital-sign data, transmit the vital-sign data to the data preprocessor to preprocess, generate a service serial number, encapsulate integrally with the data as preprocessed, and save the encapsulated data into a vital-sign database, and by the second processor of real-time analyzing and processing, read in real time data in the vital-sign database, process the data, generate the data analysis report, and send the data analysis report to the service terminal device for browsing and reading.

Exemplarily, the data invoking sub-processor is configured to, by the cloud platform, receive the data invoking instruction, resolve the instruction, authenticate user information and a validity state of user privilege that are carried by the instruction, send a response message carrying license information to the service terminal device, according to the patient information and a type of the invoked data carried by the instruction, map the service serial number of the patient, perform data retrieving and invoking, and provide the invoked data to the service terminal device for browsing, reading, real-time live broadcast, and historical playback; a record of the data invoking operation is saved into the business-information database; and the types of the invoked data include: real-time/historical vital-sign data, a data-analysis-report file, an image-video file, a multi-media video file and a medical-document file.

Exemplarily, the medical-document managing sub-processor is configured to, by the cloud platform, receive the medical-document service instruction, resolve the instruction, authenticate user information and a validity state of user privilege that are carried by the instruction, send a response message carrying license information to the service terminal device, according to the patient information and information of a type of the medical document carried by the instruction, map the service serial number of the patient, retrieve the medical document that meets the instruction parameters, and provide the medical document to the service terminal device, and by the service terminal device, perform managing operations of creating, editing, inquiring, maintaining and storing by handwriting, voice or spelling; a record of the managing operations is saved into the business-information database; and the information of the types of the medical document includes: a long-term medical advice, a temporary medical advice, a nursing form and an electronic case history.

Exemplarily, the device-remote-operation-service sub-processor is configured to, by the cloud platform, receive the device-remote-operation instruction, resolve the instruction, authenticate user information and a validity state of user privilege that are carried by the instruction, and send a response message carrying license information to the service terminal device, and simultaneously, according to information of one or more patients carried by the instruction, map IDs of one or more vital-sign monitoring devices, and retrieve and connect to devices that meet the instruction parameters, and by the service terminal device, perform operations of control measurement, state inquiring, configuration modification and equipment maintenance; the acquired operation result is saved into a corresponding database according to the data type; and a record of the device remote operation is saved into the business-information database.

Exemplarily, consultation-service sub-processor is configured to, by the cloud platform, receive the consultation initiating instruction, resolve the instruction, authenticate user information and a validity state of user privilege that are carried by the instruction, and send a response message carrying license information to the service terminal device, and simultaneously, according to patient information and consultation-party information carried by the instruction, send a notification of starting a terminal-device consultation to a consultation party, establish a data link between an initiating party and the consultation party, map the service serial number according to the patient information, share patient data, and perform multi-media video-and-data consultation; file data of the consultation information are saved into the file database; a record of the consultation operation is saved into the business-information database; and the patient data include: vital-sign data, clinical information, a data-analysis-report file, an image-video file, and a medical-document file.

Exemplarily, the medical-cooperation-information issuing sub-processor is configured to, by the cloud platform, receive the medical-cooperation-information issuing instruction, resolve the instruction, authenticate user information and a validity state of user privilege that are carried by the instruction, and send a response message carrying license information to the service terminal device, and simultaneously, according to patient information and information of a medical cooperation team that are carried by the instruction, issue cooperation information via the cloud platform to a terminal device of the medical cooperation team, and prompt by using acousto-optic effect, vibration or image-text; and a record of the medical-cooperation-information issuing operation is saved into the business-information database.

In order to meet the usage habits of different users, by using the user-self-defined-term setting sub-processor, the user can, according to the illness of the patient, set the thresholds of abnormity in a personalized manner, and set the rule configuration of system and service, the mode and range of message notification, the options of items of third-party businesses, and the user operation interface, which improves the working efficiency of the user, and can also save the record of the setting operation, which guarantees the safety of the cloud platform and the user system.

In order to facilitate the user to quickly inquire and use information on commonly used medicines, apparatuses and consumable items and medical knowledge, the medical-tool-library-service sub-processor of the cloud platform provides a medical-tool support service to the user. The medical-tool library comprises an ICU-commonly-used-medicine managing sublibrary (containing pharmacology, dosage, incompatibility, period of validity and warehouse entry time), a clinical-medicine-tool sublibrary (containing clinical-medicine dictionaries, clinical diagnosis-treatment manuals, nursing manuals and scientific literatures), and an ICU-equipment managing sublibrary (containing archives of management of apparatuses and consumable items, manuals for quick operation of defibrillators, manuals for quick operation of ventilators, and manuals for quick operation of vital-sign monitoring devices). The service terminal device may send a medical-tool-library inquiring instruction to the cloud platform, to in real time and on line quickly inquire and use the medical-tool library.

Exemplarily, the medical-tool-library-service sub-processor is configured to, by the cloud platform, receive the medical-tool-library inquiring instruction, resolve the instruction, authenticate user information and a validity state of user privilege that are carried by the instruction, send a response message carrying license information to the service terminal device, according to a type of inquired data carried by the instruction, invoke associated information in a medical-tool library, and provide to the service terminal device for browsing and reading; and a record of the medical-tool-library inquiring operation is saved into the business-information database.

Figure 2:
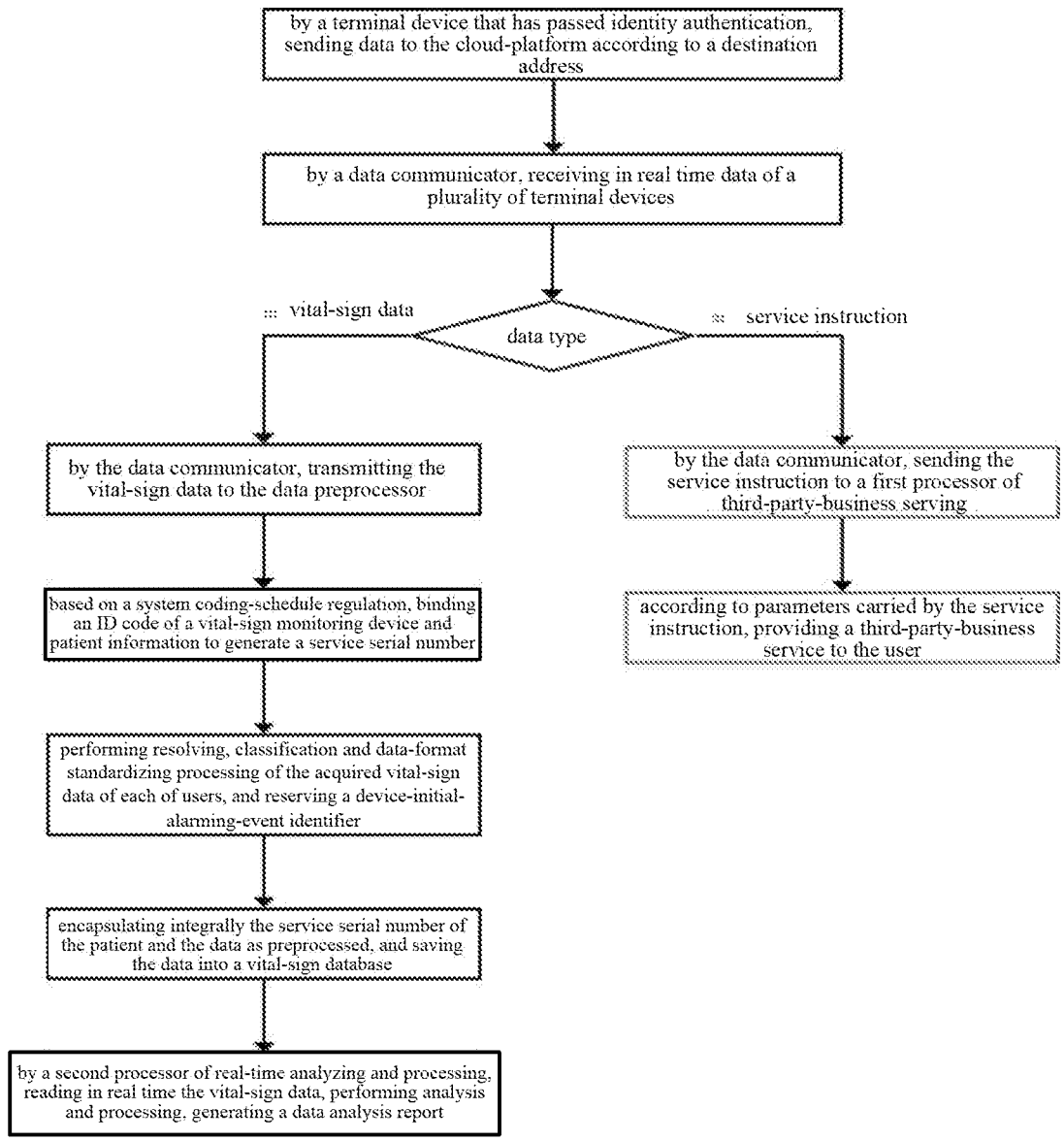
FIG. 2 is a flow chart of the method for sharing data on a medical cloud platform based on third-party business according to an embodiment of the present application.

Another embodiment of the present application discloses a method for sharing data on a medical cloud platform based on third-party business. As shown in FIG. 2, the method comprises the steps of:

Step S201, by a terminal device that has passed identity authentication, sending data to the cloud-platform according to a destination address;

Step S202, by a data communicator, receiving in real time data of a plurality of terminal devices, sending the service instruction in the data to a first processor of third-party-business serving, and transmitting the vital-sign data to the data preprocessor;

Step S203, by the data preprocessor, based on a system coding-schedule regulation, binding an ID code of a vital-sign monitoring device and patient information to generate a service serial number;

Step S204, performing resolving, classification and data-format standardizing processing of the acquired vital-sign data of each of users, and reserving a device-initial-alarming-event identifier;

Step S205, encapsulating integrally the service serial number of the patient and the data as preprocessed, and saving the encapsulated data into a vital-sign database;

Step S206, by a second processor of real-time analyzing and processing, reading in real time the vital-sign data, performing analysis and processing, and generating a data analysis report; and Step S207, by the first processor of third-party-business serving, receiving the service instruction, and according to parameters carried by the service instruction, providing a third-party-business service to the user.

As compared with the prior art, the method, by analyzing and processing in real time a massive quantity of vital-sign data, satisfies the demands of the user; by supporting the multiple communication protocols and by using the data-format standardizing processing, solves the problems of the access of external devices and systems and of non-uniform data formats, and reduces the difficulty in the concentrated and high-efficiency processing of data; by mapping the service serial number and the device ID, satisfies the requirements on the internal data inquiring of the system and the interaction with external data, and also solves the problem of identifying different patients in the same device (the same hospital bed); and by using the third-party-business service, to migrate the complicated and onerous business work of the user to the cloud platform for automatic processing, reduces the labor intensity of the medical care personnel, and improves the quality of medical care and the working efficiency.

Figure 4:
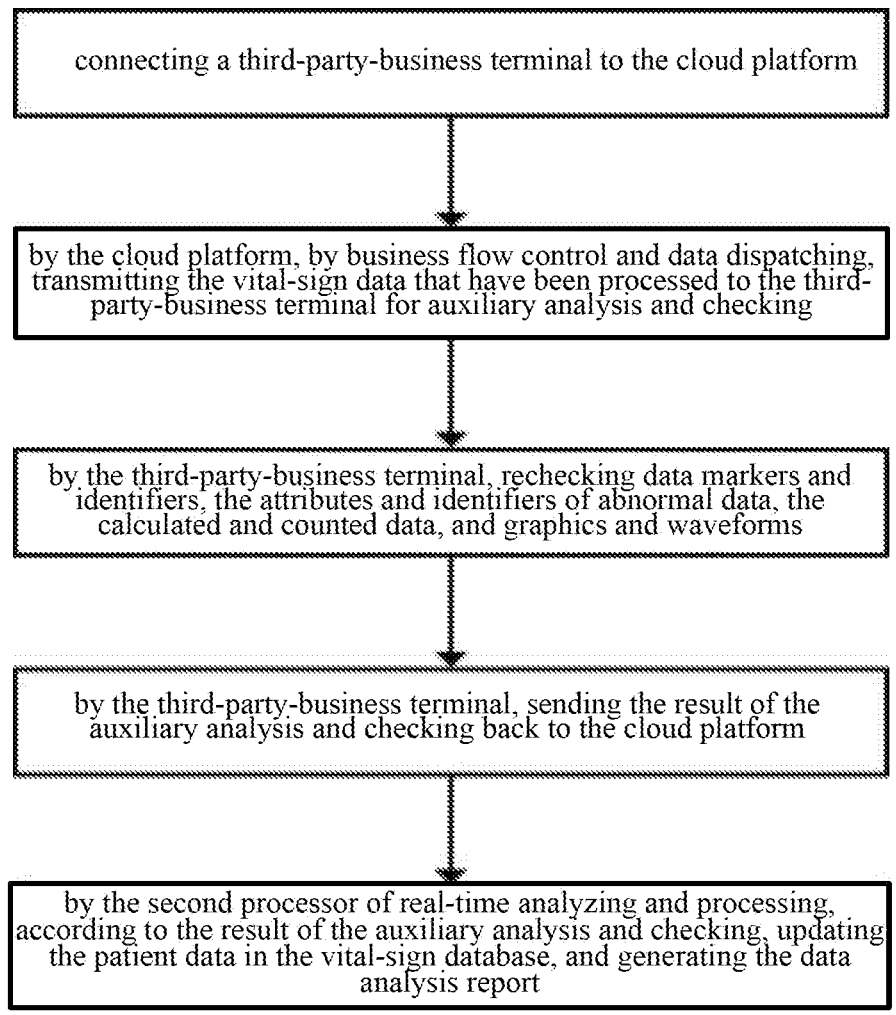
FIG. 4 is a flow chart of the auxiliary analysis and checking by a third party according to an embodiment of the present application.

In order to further improve the quality of the data analysis service of the cloud platform, particularly, as shown in FIG. 4, the method further comprises the steps of:

Step S401, connecting a third-party-business terminal to the cloud platform, and by the cloud platform, by business flow control and data dispatching, transmitting the vital-sign data that have been processed to the third-party-business terminal for auxiliary analysis and checking;

Step S402, by the third-party-business terminal, rechecking data markers and identifiers, the attributes and identifiers of abnormal data, the calculated and counted data, and graphics and waveforms;

Step S403, by the third-party-business terminal, sending the result of the auxiliary analysis and checking back to the cloud platform; and Step S404, by the second processor of real-time analyzing and processing, according to the result of the auxiliary analysis and checking, updating the patient data in the vital-sign database, and generating the data analysis report.

The process of the auxiliary analysis and processing by a third party does not only improve the accuracy and the fault tolerance of the data real-time processing and analysis of the cloud platform, but also, as the sample parameters of training of machine learning of the cloud platform, further improves the accuracy of the center model, and improves the working efficiency of the processing of the massive quantity of data.

In order to satisfy the real-time analysis and processing and abnormal-data screening of the massive quantity of vital-sign data, as shown in FIG. 3, the method further comprises the steps of:

by using the deep-learning framework of the Spark distributed parallel computation, reading the vital-sign data in the vital-sign database and the contained device-initial-alarming-event data;

wherein the Spark engine is configured to, according to a preset micro-batching time interval, create in parallel a plurality of tasks, and trigger a Spark Streaming to split the data by types into RDD data collections, and simultaneously control a center model of a corresponding type to analyze and screen the type of data;

by the center model, comprising a built-in second-order-difference calculating tool and/or logic analyzing tool, calculating and analyzing in real time the patterns, rhythms, speeds and numerical values of the vital-sign data, classifying and marking the waveforms, counting and summarizing the numerical values, and screening abnormal data that exceed a reference; and by the center model, when abnormal data that exceed a preset reference are found by the analysis and processing, analyzing features of the abnormal data, calculating a duration of an abnormal event, marking an attribute of the abnormal data, generating a real-time-data analysis report, and saving into a file database.

Optionally, the method integrates the vital-sign data of a whole process that have been analyzed and screened, outputs the vital-sign data, generates a dynamic-data analysis report, and saves the dynamic-data analysis report into a file database.

In order to improve the efficiency and accuracy of the analyzing and screening of the center model, the method further comprises, by using the quantitative and qualitative vital-sign data in the vital-sign database, training and optimizing in real time a center model of each type, to obtain a new center model of the type of data.

The waveform-type vital-sign data that are processed by using the method include: overall cardiac activity of whole process, electrocardiogram interval, QRS time limit, ST-segment evaluation pattern, QT interval, total respiration number of whole process, respiratory-wave interval, peak and trough values of pulse volume, peak and trough values of intracranial pressure, peak and trough values of partial pressure of end-tidal carbon dioxide and wave interval of partial pressure of end-tidal carbon dioxide; and the numerical-value-type vital-sign data include: systolic pressure and diastolic pressure in non-invasive/invasive blood pressure, pulse rate, oxyhemoglobin saturation, body temperature and fetal heart rate of whole process; stroke volume, cardiac index and total value of peripheral resistance of non-invasive heart stroke; and value of airway pressure, value of airway flow rate and value of airway volume of respiratory mechanics.

The features of abnormal data that are analyzed by using the method include: tachycardia, bradycardia, flutter-fibrillation, frequent premature beat, cardiac arrest, RonT, QT interval extension, ST-segment rising/descending, apnea, bradypnea, tachypnoea, rising/descending of oxyhemoglobin saturation, rising/descending of systolic pressure and diastolic pressure, rising/descending of mean arterial pressure, rising/descending of peak value of pulse volume, rising/descending of peak value of intracranial pressure, rising/descending of peak value of partial pressure of end-tidal carbon dioxide, rising/descending of fetal heart rate, descending of non-invasive heart stroke, and rising/descending of values of respiratory mechanics.

The contents of the dynamic-data analysis report that is generated by using the method include: for the whole process, comprehensive analysis and calculation, classification and marking of waveforms and oscillograms of data of dynamic electrocatdiogram, data of dynamic blood pressure, data of respiration, data of oxyhemoglobin saturation, data of invasive blood pressure, data of intracranial pressure, data of partial pressure of end-tidal carbon dioxide, data of body temperature, data of non-invasive heart stroke, and data of respiratory mechanics, and their tendency charts, histograms, scatter plots, and diagrams of variability analysis.

The contents of the real-time-data analysis report that is generated by using the method include: real-time analysis and calculation, classification and marking of waveforms, and abnormal oscillograms of data of abnormal electrocatdiogram, data of abnormal blood pressure, data of abnormal respiration, data of abnormal oxyhemoglobin saturation, data of abnormal intracranial pressure, data of abnormal partial pressure of end-tidal carbon dioxide, data of abnormal body temperature, data of abnormal fetal heart rate, data of abnormal non-invasive heart stroke, and data of abnormal respiratory mechanics, and their tendency charts.

The cloud platform saves the above data analysis reports into the file database, and the user may send a data invoking instruction to the cloud platform, to perform retrieving, inquiring, statistical analysis, reviewing and summarizing.

Figure 5:
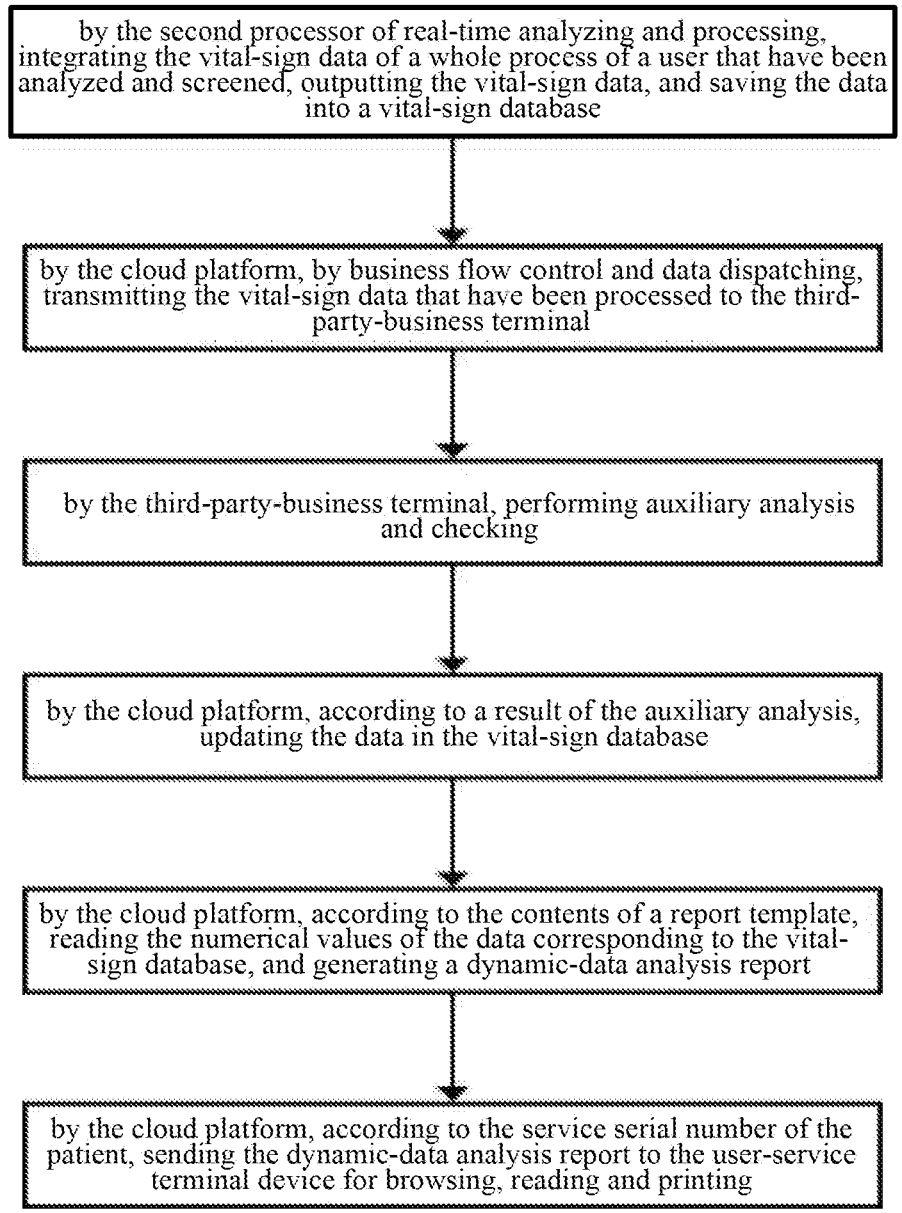
FIG. 5 is a flow chart of the generation of the dynamic-data analysis report according to an embodiment of the present application.

In order to facilitate the user to evaluate the variation of the illness of the patient, and summarize the clinical medical effects, and also in order to facilitate the user to browse and read, save the diagnosis and treatment durations, and alleviate the working load of the medical care personnel, when the length of the routine data that are analyzed and processed by the cloud platform is greater than a preset data length, a process of dynamic-data analysis report is triggered. As shown in FIG. 5, the method particularly comprises the steps of:

Step S501, by the cloud platform, by using second processor of real-time analyzing and processing, integrating the vital-sign data of a whole process of a user that have been analyzed and screened, outputting the vital-sign data, and saving the data into a vital-sign database;

Step S502, by the cloud platform, by business flow control and data dispatching, transmitting the vital-sign data that have been processed to the third-party-business terminal for auxiliary analysis and checking;

Step S503, by the cloud platform, according to a result of the auxiliary analysis, updating the data in the vital-sign database;

Step S504, by the cloud platform, according to the contents of a report template, reading the numerical values of the data corresponding to the vital-sign database, and generating a dynamic-data analysis report; and Step S505, by the cloud platform, according to the service serial number of the patient, sending the dynamic-data analysis report to the user-service terminal device for browsing, reading and printing.

Further, the service terminal device inputs the service-instruction parameters, logs in on the cloud platform, sends the service instruction, obtains the response from the cloud platform, and provides the third-party-business service. The third-party-business service includes: a real-time-data service, a data invoking service, a medical-document managing service, a consultation service, a patient-state evaluating service, a device-remote-operation service, a medical-cooperation-information issuing service, a user-self-defined-term setting service, a data-analysis-report managing service and a medical-tool-library managing service.

Figure 6:
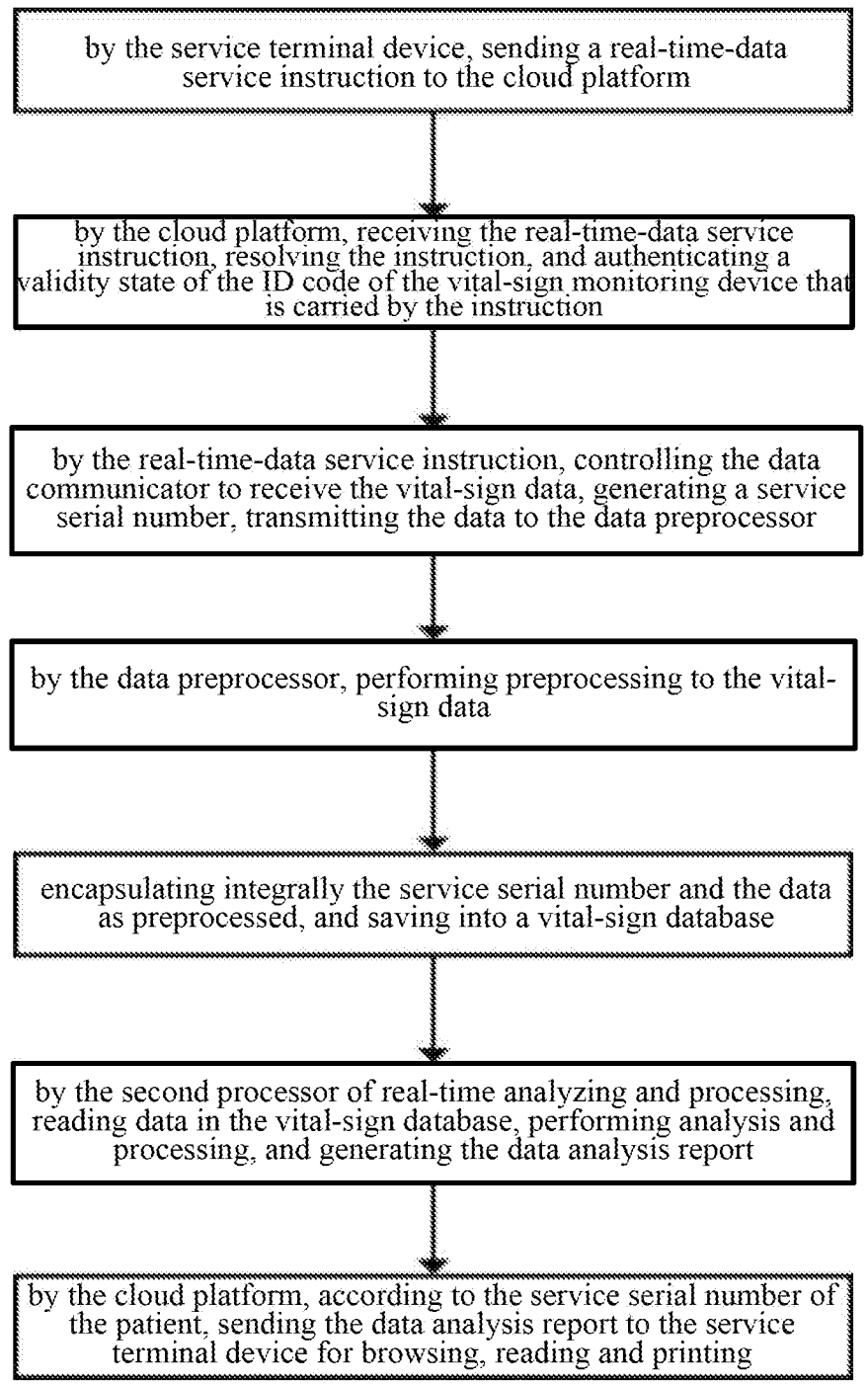
FIG. 6 is a flow chart of the real-time-data service according to an embodiment of the present application.

Exemplarily, in order to solve the problem of the difficulty in the analysis and interpretation of the vital-sign data of the user, a real-time-data service is provided to the user. As shown in FIG. 6, the method comprises the steps of:

Step S601, by the service terminal device, sending a real-time-data service instruction to the cloud platform;

Step S602, by the cloud platform, receiving the real-time-data service instruction, resolving the instruction, and authenticating a validity state of the ID code of the vital-sign monitoring device that is carried by the instruction;

Step S603, by the instruction, controlling the data communicator to receive the vital-sign data, transmitting the vital-sign data to the data preprocessor to preprocess, generating a service serial number, encapsulating integrally with the data as preprocessed, and saving the encapsulated data into a vital-sign database;

Step S604, by the second processor of real-time analyzing and processing, reading data in the vital-sign database, performing analysis and processing, and generating the data analysis report; and Step S605, by the cloud platform, according to the service serial number of the patient, sending the data analysis report to the service terminal device for browsing, reading and printing.

Figure 7:
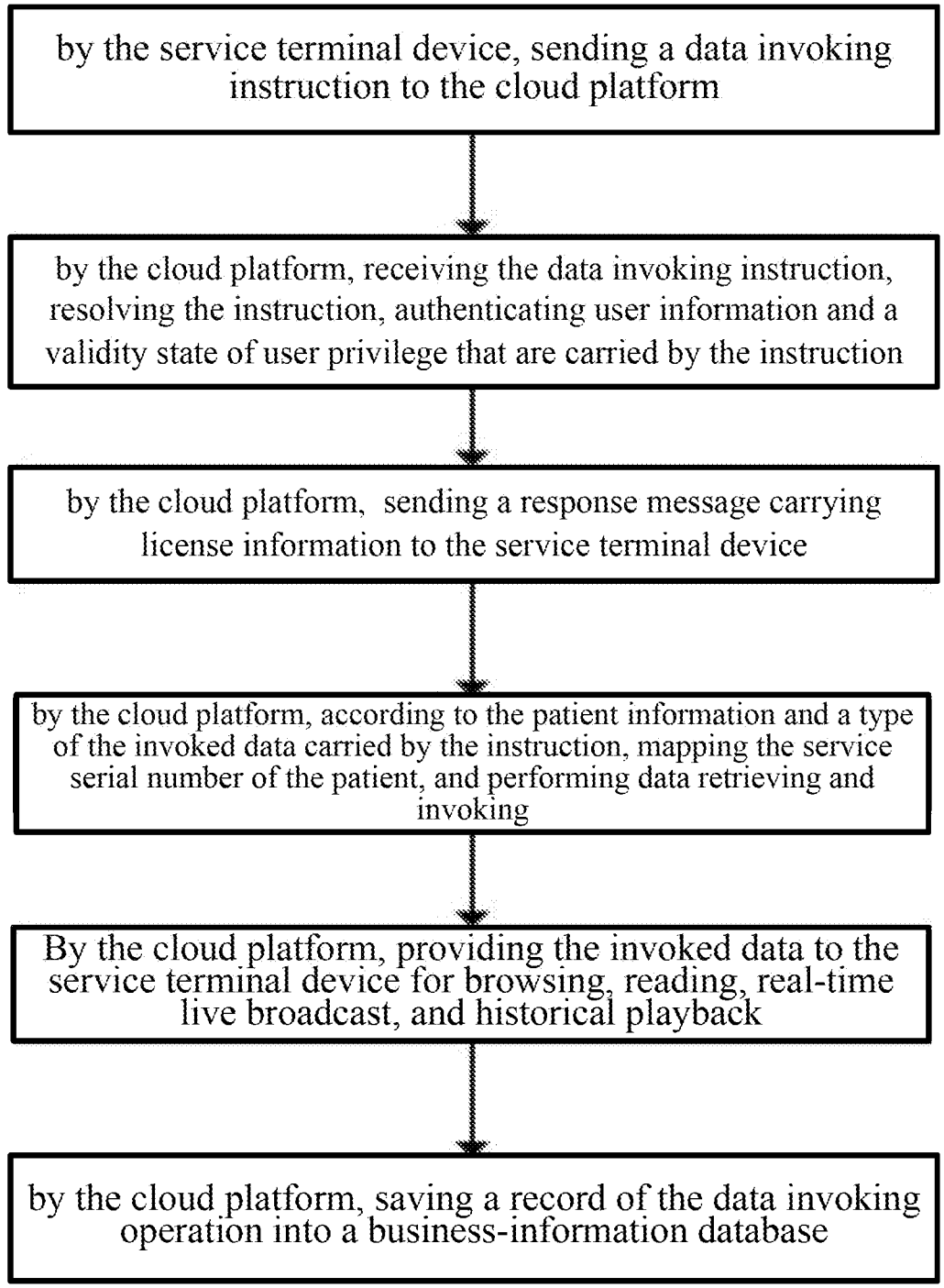
FIG. 7 is a flow chart of the data invoking service according to an embodiment of the present application.

Exemplarily, in order to facilitate the user to acquire and read the real-time data and the historical data at any time, a data invoking service is provided. As shown in FIG. 7, the method comprises the steps of:

Step S701, by the service terminal device, sending a data invoking instruction to the cloud platform;

Step S702, by the cloud platform, receiving the data invoking instruction, resolving the instruction, authenticating user information and a validity state of user privilege that are carried by the instruction, and sending a response message carrying license information to the service terminal device;

Step S703, by the cloud platform, according to the patient information and a type of the invoked data carried by the instruction, mapping the service serial number of the patient, and performing data retrieving and invoking;

Step S704, by the cloud platform, providing the invoked data to the service terminal device for browsing, reading, real-time live broadcast, and historical playback; and Step S705, by the cloud platform, saving a record of the data invoking operation into a business-information database; wherein the invoked data include: real-time/historical vital-sign data, a data-analysis-report file, an image-video file, a multi-media video file and a medical-document file.

Figure 8:
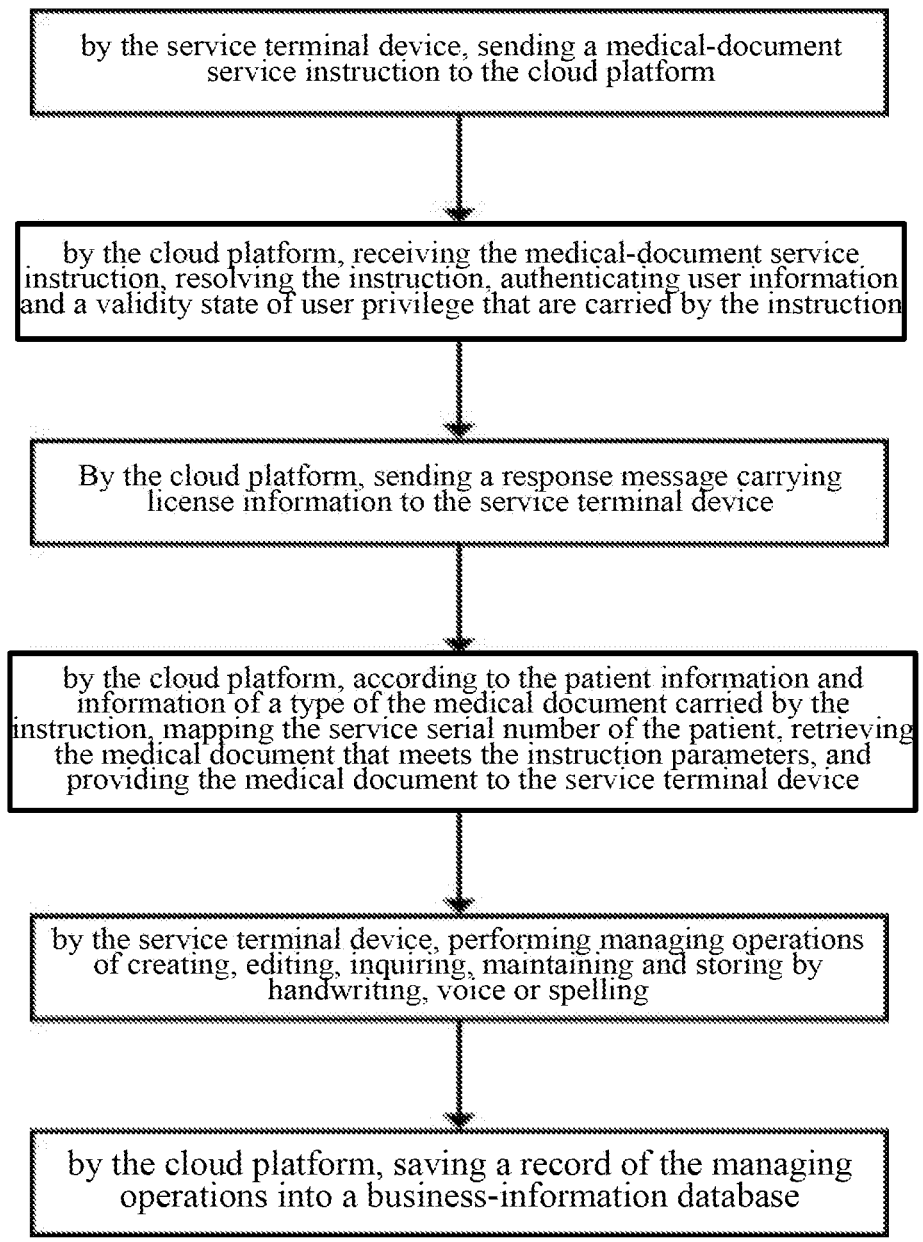
FIG. 8 is a flow chart of the medical-document managing service according to an embodiment of the present application.

Exemplarily, in order to support the electronization of medical documents of the user, and reduce the labor intensity and the working pressure of the medical care personnel, a medical-document managing service is provided. As shown in FIG. 8, the method comprises the steps of:

Step S801, by the service terminal device, sending a medical-document service instruction to the cloud platform;

Step S802, by the cloud platform, receiving the medical-document service instruction, resolving the instruction, authenticating user information and a validity state of user privilege that are carried by the instruction, and sending a response message carrying license information to the service terminal device;

Step S803, by the cloud platform, according to the patient information and information of a type of the medical document carried by the instruction, mapping the service serial number of the patient, retrieving the medical document that meets the instruction parameters, and providing the medical document to the service terminal device;

Step S804, by the service terminal device, performing managing operations of creating, editing, inquiring, maintaining and storing by handwriting, voice or spelling; and Step S805, by the cloud platform, saving a record of the managing operations into a business-information database; wherein the information of the types of the medical document includes: a long-term medical advice, a temporary medical advice, a nursing form and an electronic case history.

Figure 9:
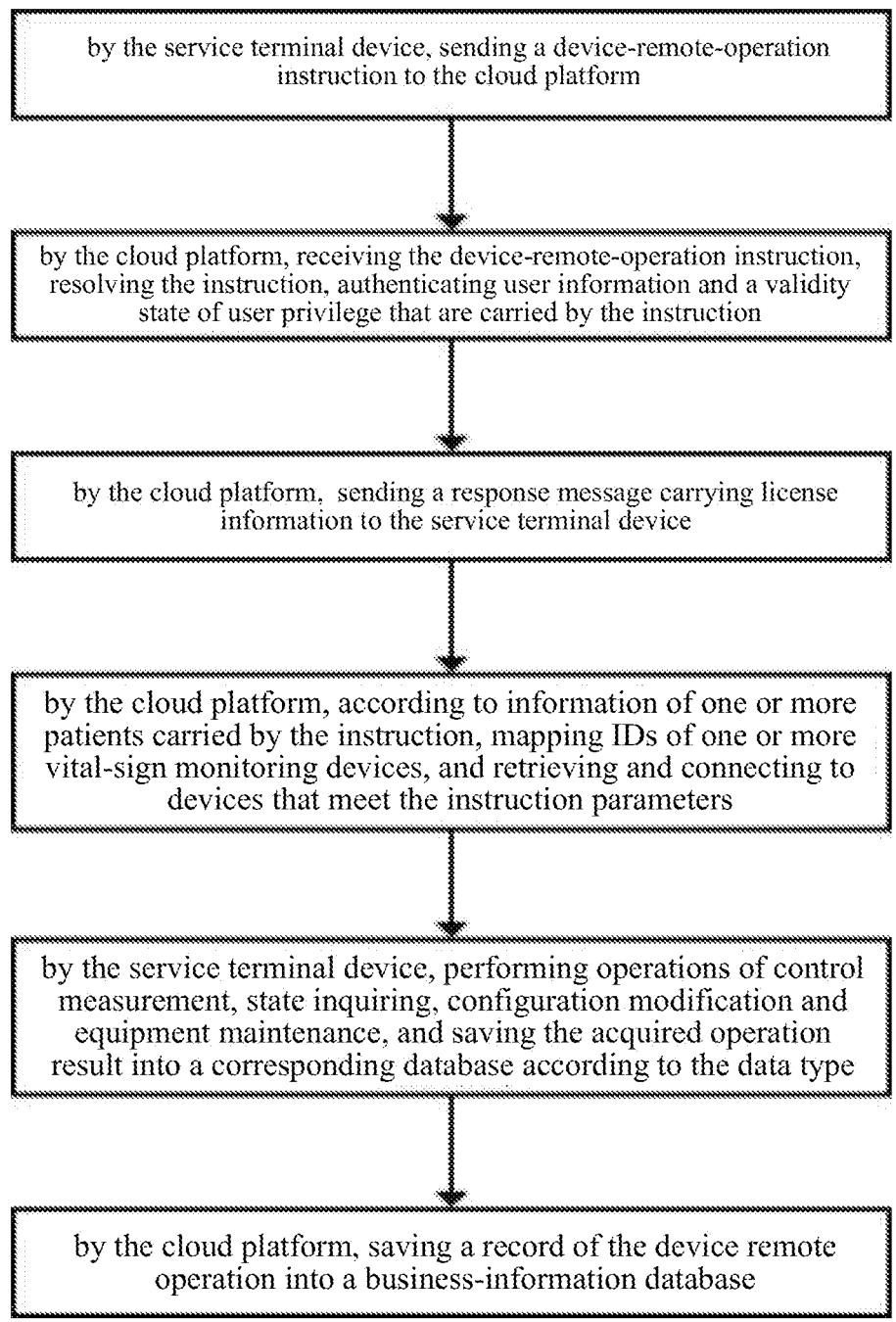
FIG. 9 is a flow chart of the device-remote-operation service according to an embodiment of the present application.

Exemplarily, in order to support various application scenes of the user, a device-remote-operation service is provided. As shown in FIG. 9, the method comprises the steps of:

Step S901, by the service terminal device, sending a device-remote-operation instruction to the cloud platform;

Step S902, by the cloud platform, receiving the device-remote-operation instruction, resolving the instruction, authenticating user information and a validity state of user privilege that are carried by the instruction, and sending a response message carrying license information to the service terminal device;

Step S903, by the cloud platform, according to information of one or more patients carried by the instruction, mapping IDs of one or more vital-sign monitoring devices, and retrieving and connecting to devices that meet the instruction parameters;

Step S904, by the service terminal device, performing operations of control measurement, state inquiring, configuration modification and equipment maintenance, and saving the acquired operation result into a corresponding database according to the data type; and Step S905, by the cloud platform, saving a record of the device remote operation into a business-information database.

Figure 10:
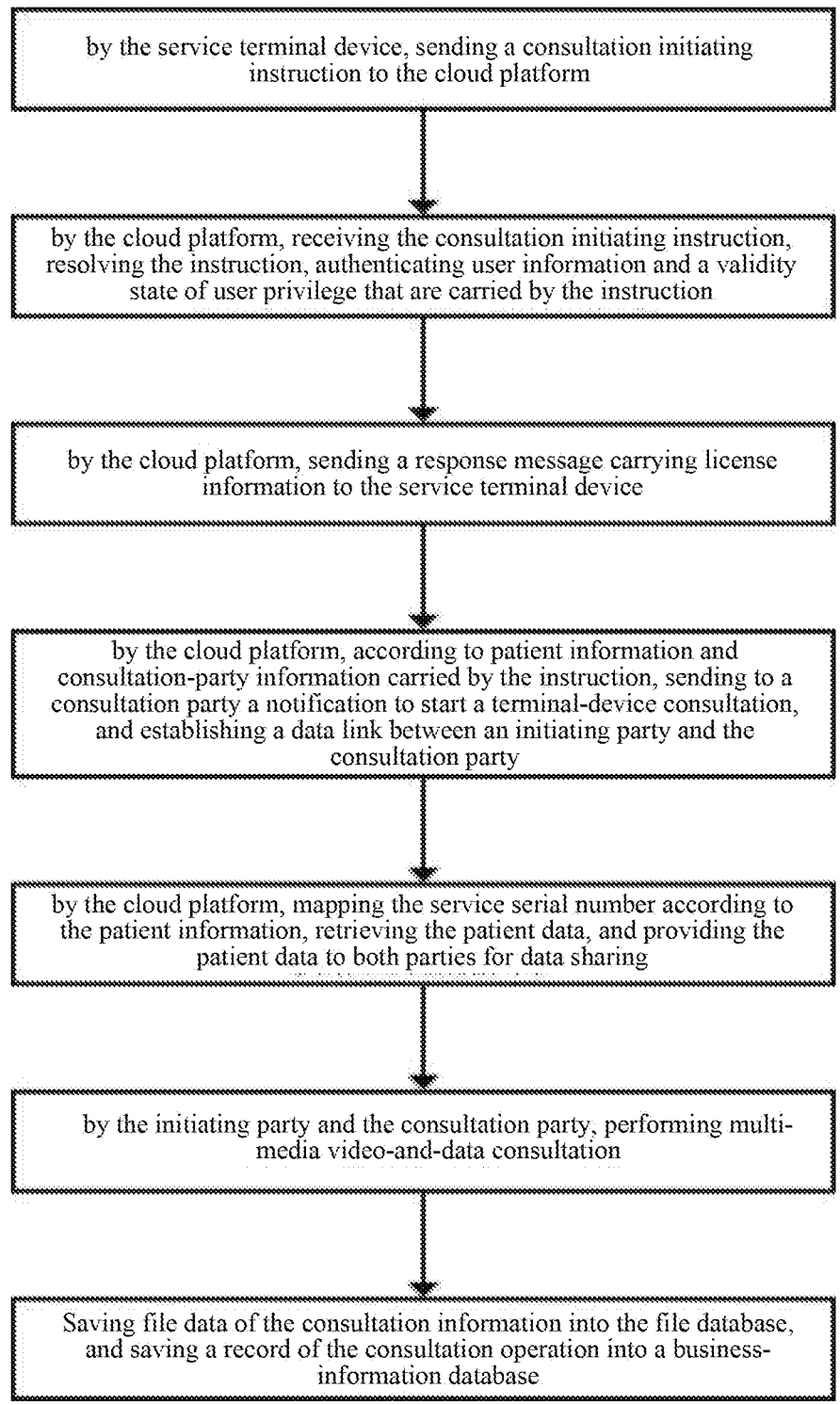
FIG. 10 is a flow chart of the consultation service according to an embodiment of the present application.

Exemplarily, in order to sufficiently use high-quantity medical resources and improve the quality of medical service, a data-sharing consultation service between users is provided. As shown in FIG. 10, the method comprises the steps of:

Step S1001, by the service terminal device, sending a consultation initiating instruction to the cloud platform;

Step S1002, by the cloud platform, receiving the consultation initiating instruction, resolving the instruction, authenticating user information and a validity state of user privilege that are carried by the instruction, and sending a response message carrying license information to the service terminal device;

Step S1003, by the cloud platform, according to patient information and consultation-party information carried by the instruction, sending a notification of starting a terminal-device consultation to a consultation party, and establishing a data link between an initiating party and the consultation party;

Step S1004, by the cloud platform, mapping the service serial number according to the patient information, retrieving the patient data, and providing the patient data to both parties for data sharing;

Step S1005, by the initiating party and the consultation party, performing multi-media video-and-data consultation; and Step S1006, saving file data of the consultation information into the file database, and saving a record of the consultation operation into a business-information database; wherein the data include: vital-sign data, clinical information, data of a data-analysis-report file, data of an image-video file, and data of a medical-document file.

Figure 11:
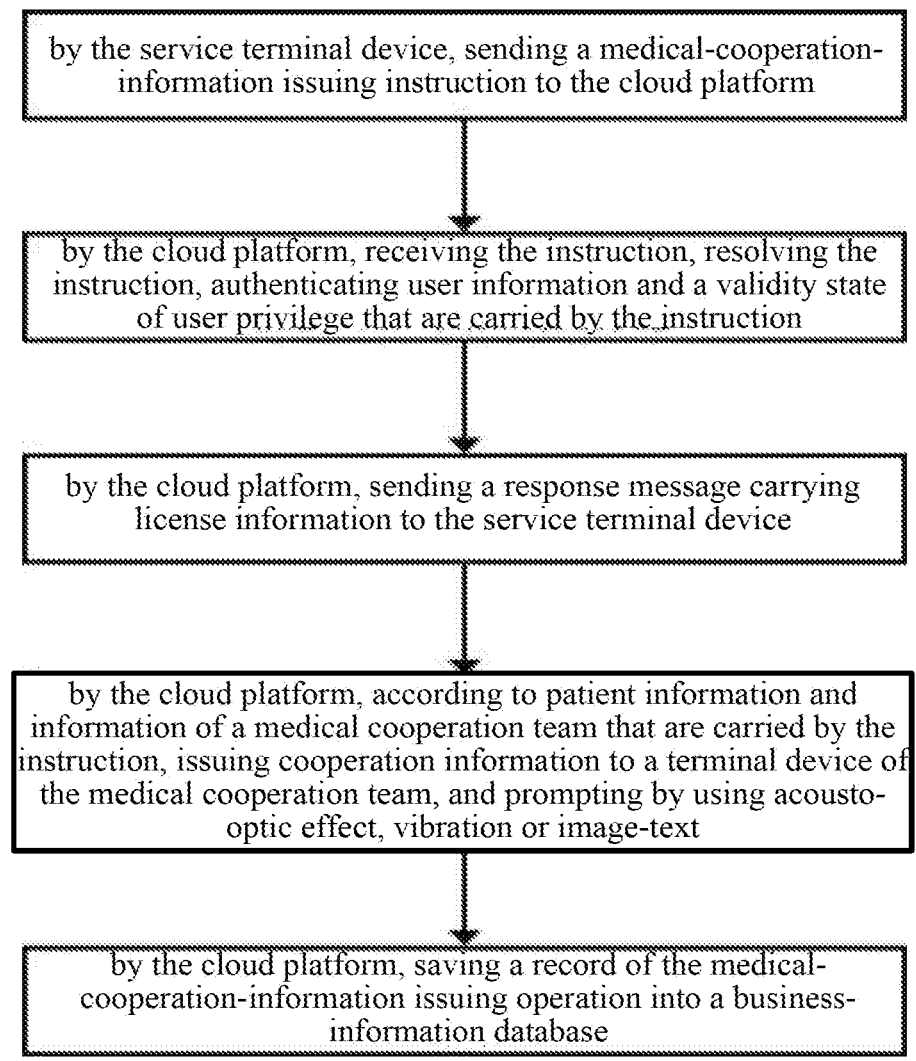
FIG. 11 is a flow chart of the medical-cooperation-information issuing service according to an embodiment of the present application.

Exemplarily, in order to support the user to quickly concentrate medical resources to serve patients of emergency treatment and high-risk intractable patients, a medical-cooperation-information issuing service is provided. As shown in FIG. 11, the method comprises the steps of:

Step S1101, by the service terminal device, sending a medical-cooperation-information issuing instruction to the cloud platform;

Step S1102, by the cloud platform, receiving the instruction, resolving the instruction, authenticating user information and a validity state of user privilege that are carried by the instruction, and sending a response message carrying license information to the service terminal device;

Step S1103, by the cloud platform, according to patient information and information of a medical cooperation team that are carried by the instruction, issuing cooperation information to a terminal device of the medical cooperation team, and prompting by using acousto-optic effect, vibration or image-text; and Step S1104, by the cloud platform, saving a record of the medical-cooperation-information issuing operation into a business-information database.

In order to meet the usage habits of different users, the users, by using the user-self-defined-term setting sub-processor of the cloud platform, according to the illness of the patient, may set the thresholds of abnormity in a personalized manner, and set the rule configuration of system and service, the mode and range of message notification, the options of items of third-party businesses, and the user operation interface, which improves the working efficiency of the user, and may also save the record of the setting operation, which guarantees the safety of the cloud platform and the user system.

In order to facilitate the user to quickly inquire and use information on commonly used medicines, apparatuses and consumable items and medical knowledge, the medical-tool-library-service sub-processor of the cloud platform provides a medical-knowledge-library service to the user. The medical-tool library comprises an ICU-commonly-used-medicine managing sublibrary (containing pharmacology, dosage, incompatibility, period of validity and warehouse entry time), a clinical-medicine-tool sublibrary (containing clinical-medicine dictionaries, clinical diagnosis-treatment manuals, nursing manuals and scientific literatures), and an ICU-equipment managing sublibrary (containing archives of management of apparatuses and consumable items, manuals for quick operation of defibrillators, manuals for quick operation of ventilators, and manuals for quick operation of vital-sign monitoring devices). The service terminal device may send a service instruction to the cloud platform, to in real time and on line quickly inquire and use the medical-tool library.

The present disclosure, by using the functions of the cloud platform of managing the service objects and attributes, and managing the relation between the roles of the service objects, determines the natures, levels and roles of users in the business operation, establishes a close relation of upper and lower levels between large-scale hospitals and small and medium-scale hospitals, and realizes on the cloud platform the sharing of medical data and medical resources, the consultation of high-risk intractable cases, and remote teaching and ward inspection, which improves the medical proficiency of the small and medium-scale hospitals. By using the data-analysis-report managing service of the cloud platform, the user can, by using the terminal device, quickly and conveniently retrieve and use the data analysis report, as the clinical medical basis for evaluating medical effects. By the data analyzing and counting service, the cloud platform provides to the user an universal medical statistical tool, whereby various business data can be analyzed and counted, and the result can be provided to the terminal device of the user for browsing and reading. By the patient-state evaluating service, the cloud platform provides to the user an universal severe-illness evaluation system model, by automatically gathering the vital-sign data and the relative indexes of the patient in the database, and evaluating and predicting the disease state and the developing trend of the patient, which supports the digitalization of the routine work of the user, reduces the working pressure of the user, and improves the quality of medical care. Either of the first processor, the second processor is independent processor, or both processors are integrated in a single processor. Each of sub-processors is independent sub-processor, or these sub-processors are integrated in a single sub-processor.

It should be noted that the system and method for sharing data on a medical cloud platform based on third-party business of the present application may be deployed, implemented and operated in a public cloud or a private cloud, and may be implemented by using a server, a database or an application service system at the cloud side.

The above method embodiments and system embodiments are based on the same or similar principles, and the similar features of them may refer to each other, to obtain the same effects.

A person skilled in the art can understand that all or part of the process of implementing the methods of the above embodiments may be implemented by related hardware according to an instruction from a computer program, and the program may be stored in a computer-readable storage medium, wherein the computer-readable storage medium is a magnetic disc, an optical disc, a read-only memory, a random access memory and so on.

The above are merely preferable particular embodiments of the present application, and the protection scope of the present application is not limited thereto. All of the variations or substitutions that a person skilled in the art can easily envisage within the technical scope disclosed by the present application should fall within the protection scope of the present application.

What is claimed is:

1. A system for sharing data on a medical cloud platform based on third-party business, comprising: a terminal device and a cloud platform;

the cloud platform comprises: a cloud-platform data communication subsystem, a cloud-platform data support subsystem and a cloud-platform third-party-business subsystem;

wherein the cloud-platform data communication subsystem is configured for data communication between the cloud-platform third-party-business subsystem and the terminal device;

wherein the cloud-platform data support subsystem is configured to, by applying a deep-learning framework of distributed parallel computation, process and store in real time data received by the cloud-platform;

wherein the cloud-platform third-party-business subsystem is configured to provide third-party business according to a service requesting instruction of the terminal device, and is further configured to perform auxiliary analysis and checking of abnormal data that are processed by the cloud-platform data support subsystem; and the terminal device comprises: a service terminal device and a vital-sign monitoring device of ICUs, and is configured to send data to the cloud-platform according to a destination address, and receive service of the third-party business;

wherein the data comprise: a service instruction and vital-sign data;

the cloud-platform data communication subsystem comprises: a data communicator and a data preprocessor;

the data communicator is configured to receive in real time data of a plurality of terminal devices, and perform data interaction with a user, send the service instruction in the data to the cloud-platform third-party-business subsystem, and transmit the vital-sign data to the data preprocessor;

the data preprocessor is configured to bind an ID code of a vital-sign monitoring device and patient information to generate a service serial number, and simultaneously perform resolving, classification and data-format standardizing processing of the vital-sign data, reserve a device-initial-alarming-event identifier, encapsulate integrally the service serial number and the vital-sign data as preprocessed, and save the encapsulated data into a vital-sign database;

the cloud-platform third-party-business subsystem comprises a first processor of third-party-business serving and a third-party-business terminal; the first processor of third-party-business serving is configured to receive the service instruction, and provide a third-party-business service to the user; and the third-party-business terminal is configured for the auxiliary analysis and checking of the vital-sign data of the cloud platform;

the cloud-platform data support subsystem comprises: a message bus, a data storage and a second processor of real-time analyzing and processing;

the message bus is configured to connect and control data transmission among the subsystems and the processors, the message bus, the data storage, the data communicator and the data preprocessor of the cloud platform;

the data storage comprises the vital-sign database, a file database, a business-information database and a buffer database, and is configured for storing and invoking of the data; and the second processor of real-time analyzing and processing is configured to read in real time data in the vital-sign database, perform analysis and processing, generate a data analysis report, and send the data analysis report to the service terminal device for browsing and reading, and simultaneously save the data analysis report into the file database;

wherein the second processor of real-time analyzing and processing is configured to perform real-time analysis and screening of the vital-sign data by using a mode of on-line real-time data analysis and processing and a deep-learning framework based on Spark engine;

the deep-learning framework of the Spark distributed parallel computation is configured to read in real time the vital-sign data in the vital-sign database, wherein the Spark engine is configured to, according to a preset micro-batching time interval, create in parallel a plurality of tasks, and trigger a Spark Streaming to split the data by types into RDD data collections, and simultaneously control a center model of a corresponding type to calculate and process the type of data; and the center model is configured to, when abnormal data that exceed a preset reference are found by the calculating and processing, analyze features of the abnormal data, calculate a duration, and mark an attribute of the abnormal data;

the second processor of real-time analyzing and processing is configured to generate a real-time-data analysis report from the abnormal data, and send an abnormal-event warning to the user;

the second processor of real-time analyzing and processing is configured to integrate the vital-sign data of a whole process of a user that have been analyzed and screened, and generate a dynamic-data analysis report; and the second processor of real-time analyzing and processing is configured to, by using the vital-sign data that have been analyzed and screened, train and optimize in real time a center model of each type, to obtain a new center model of the type of data.

2. The system according to claim 1, wherein the third-party-business terminal is connected to the cloud platform, and is configured to perform real-time auxiliary analysis and checking of the vital-sign data that have been in real time analyzed and processed, and the second processor of real-time analyzing and processing is configured to, according to a result of the auxiliary analysis, update the data in the vital-sign database, and use the data to generate the data analysis report.

3. The system according to claim 1, wherein the service instruction is formed by an instruction name and a parameter, and comprises: a real-time-data service instruction, a data invoking instruction, an abnormal-data-event inquiring instruction, a data-analysis-report managing instruction, a medical-document service instruction, a data analyzing and counting instruction, a user-self-defined-term setting instruction, a consultation initiating instruction, a patient-state evaluating instruction, a device-remote-operation instruction, a medical-cooperation-information issuing instruction, and a medical-tool-library inquiring instruction.

4. The system according to claim 1, wherein the first processor of third-party-business serving comprises a real-time-data-service sub-processor; and the real-time-data-service sub-processor is configured to receive the real-time-data service instruction, resolve the instruction, authenticate a validity state of the ID code of the vital-sign monitoring device that is carried by the instruction, control the data communicator to receive the vital-sign data, transmit the vital-sign data to the data preprocessor to preprocess, generate a service serial number, encapsulate integrally with the data as preprocessed, save the encapsulated data into a vital-sign database, provide to the second processor of real-time analyzing and processing to be in real time analyzed and processed, generate the data analysis report, and send the data analysis report to the service terminal device for browsing and reading.

5. The system according to claim 1, wherein the first processor of third-party-business serving comprises a data invoking sub-processor; the data invoking sub-processor is configured to receive the data invoking instruction, resolve the instruction, authenticate user information and a validity state of user privilege that are carried by the instruction, send a response message carrying license information to the service terminal device, according to the patient information and a type of the invoked data carried by the instruction, map the service serial number of the patient, perform data retrieving and invoking, and provide the invoked data to the service terminal device for browsing, reading, real-time live broadcast, and historical playback; a record of the data invoking operation is saved into the business-information database; and the types of the data comprise: real-time data and historical data.

6. The system according to claim 1, wherein the first processor of third-party-business serving comprises a medical-document managing sub-processor; the medical-document managing sub-processor is configured to receive the medical-document service instruction, resolve the instruction, authenticate user information and a validity state of user privilege that are carried by the instruction, send a response message carrying license information to the service terminal device, according to the patient information and information of a type of the medical document carried by the instruction, map the service serial number of the patient, and retrieve and select a medical document that meets the instruction parameters, and the service terminal device performs managing operations of creating, editing, inquiring, maintaining and storing by handwriting, voice or spelling; a record of the managing operations is saved into the business-information database; and the types of the medical document comprise: a medical advice, a nursing form and an electronic case history.

7. The system according to claim 1, wherein the first processor of third-party-business serving comprises a user-self-defined-term setting sub-processor; the user-self-defined-term setting sub-processor is configured to receive the user-self-defined-term setting instruction, resolve the instruction, authenticate user information and a validity state of user privilege that are carried by the instruction, send a response message carrying license information to the service terminal device, and permit the user to edit, update and store the user-self-defined term, and the cloud platform executes the setting as updated; a record of the setting operation is saved into the business-information database; and the user-self-defined term comprises: a rule configuration of system and service, a mode and range of message notification, options of items of third-party businesses, and setting of a user operation interface.

8. The system according to claim 1, wherein the first processor of third-party-business serving comprises a device-remote-operation-service sub-processor; the device-remote-operation-service sub-processor is configured to receive the device-remote-operation instruction, resolve the instruction, authenticate user information and a validity state of user privilege that are carried by the instruction, and send a response message carrying license information to the service terminal device, and simultaneously, according to information of one or more patients carried by the instruction, map IDs of one or more vital-sign monitoring devices, and retrieve and connect to devices that meet the instruction parameters, and the service terminal device regulates a working mode of the vital-sign monitoring device by remote control; the acquired result is saved into a corresponding database according to the data type; and a record of the device remote operation is saved into the business-information database.

9. The system according to claim 1, wherein the first processor of third-party-business serving comprises a consultation-service sub-processor; the consultation-service sub-processor is configured to receive the consultation initiating instruction, resolve the instruction, authenticate user information and a validity state of user privilege that are carried by the instruction, and send a response message carrying license information to the service terminal device, and simultaneously, according to patient information and consultation-party information carried by the instruction, send a notification of starting a terminal-device consultation to a consultation party via the cloud platform, establish a data link between an initiating party and the consultation party, according to the patient information, map the service serial number, share patient data, and perform multi-media video-and-data consultation; file data of the consultation information are saved into the file database; and a record of the consultation operation is saved into the business-information database.

10. The system according to claim 1, wherein the first processor of third-party-business serving comprises a medical-cooperation-information issuing sub-processor; the medical-cooperation-information issuing sub-processor is configured to receive the medical-cooperation-information issuing instruction, resolve the instruction, authenticate user information and a validity state of user privilege that are carried by the instruction, and send a response message carrying license information to the service terminal device, and simultaneously, according to patient information and information of a medical cooperation team that are carried by the instruction, issue cooperation information via the cloud platform to a terminal device of the medical cooperation team, and prompt by using acousto-optic effect, vibration or image-text; and a record of the issuing operation is saved into the business-information database.

11. The system according to claim 1, wherein the first processor of third-party-business serving comprises a medical-tool-library-service sub-processor; the medical-tool-library-service sub-processor is configured to receive the medical-tool-library inquiring instruction, resolve the instruction, authenticate user information and a validity state of user privilege that are carried by the instruction, send a response message carrying license information to the service terminal device, according to a type of inquired data carried by the instruction, invoke associated information in a medical-tool library, and provide to the service terminal device for browsing and reading; a record of the medical-tool-library inquiring operation is saved into the business-information database; and the medical-tool library comprises an ICU-commonly-used-medicine managing sublibrary, a clinical-medicine-tool sublibrary, and an ICU-equipment managing sublibrary.

12. A method for sharing data on a medical cloud platform based on third-party business, comprising:
    by a terminal device that has passed identity authentication, sending data to the cloud-platform according to a destination address;
    by a data communicator, receiving in real time data of a plurality of terminal devices, wherein the data comprise: a service instruction and vital-sign data, sending the service instruction to a first processor of third-party-business serving, and transmitting the vital-sign data to the data preprocessor;

by the first processor of third-party-business serving, receiving the service instruction, and according to parameters carried by the service instruction, providing a third-party-business service to the user;

by the data preprocessor, based on a system coding-schedule regulation, binding an ID code of a vital-sign monitoring device of ICUs and patient information to generate a service serial number;

performing resolving, classification and data-format standardizing processing of the acquired vital-sign data of each of users, and reserving a device-initial-alarming-event identifier;

encapsulating integrally the service serial number of the patient and the data as preprocessed, and saving the encapsulated data into a vital-sign database; and by a second processor of real-time analyzing and processing, reading in real time the vital-sign data, performing analysis and processing of the vital-sign data, and generating a data analysis report;

wherein the third-party-business service comprises a real-time-data service, and a process of the real-time-data service comprises the steps of:

by the service terminal device, inputting patient information and an ID code of the vital-sign monitoring device, and sending a real-time-data service instruction to the cloud platform;

by the data communicator, sending the received instruction to a real-time-data-service sub-processor;

by the real-time-data-service sub-processor, receiving the instruction, resolving the instruction, authenticating and verifying a validity state of the ID code of the vital-sign monitoring device carried by the instruction, sending a response message carrying license information to the data communicator, permitting to receive the vital-sign data, and transmitting to the data preprocessor;

by the data preprocessor, performing preprocessing to the vital-sign data, generating a service serial number, encapsulating integrally the service serial number and the vital-sign data as preprocessed, and saving the encapsulated data into a vital-sign database;

by the second processor of real-time analyzing and processing, reading in real time the vital-sign data in the vital-sign database by using a mode of on-line real-time data analysis and processing and a deep-learning framework based on Spark engine, wherein the Spark engine is configured to, according to a preset micro-batching time interval, create in parallel a plurality of tasks, and trigger a Spark Streaming to split the data by types into RDD data collections, and simultaneously control a center model of a corresponding type to calculate and process the type of data;

by the center model, finding abnormal data that exceed a preset reference, analyzing features of the abnormal data, calculating a duration of an abnormal event, and marking an attribute of the abnormal data;

by the second processor of real-time analyzing and processing, generating a real-time-data analysis report according to the abnormal data, sending an abnormal-event warning to the user, sending the analysis report to the service terminal device, and saving the analysis report into a file database;

by the second processor of real-time analyzing and processing, integrating the vital-sign data of a whole process of a user that have been analyzed and screened, generating a dynamic-data analysis report, sending the dynamic-data analysis report to the service terminal device, and saving the dynamic-data analysis report into a file database;

by the second processor of real-time analyzing and processing, by using the vital-sign data that have been analyzed and screened in the vital-sign database, training and optimizing in real time a center model of each type, to obtain a new center model of the type of data; and by a third-party-business terminal, performing real-time auxiliary analysis and checking of the vital-sign data that have been processed, and by the second processor of real-time analyzing and processing, according to a result of the auxiliary analysis, updating the data in the vital-sign database, and using the data to generate the data analysis report.

13. The method according to claim 12, wherein the third-party-business service further comprises a data invoking service, and a process of the data invoking service comprises the steps of:

by the service terminal device, inputting patient information and information of type of invoked data, and sending a data-invoking-service instruction to the cloud platform;

by the data communicator, sending the received instruction to a data-invoking-service sub-processor;

by the data-invoking-service sub-processor, receiving the instruction, resolving the instruction, authenticating user information and a validity state of user privilege that are carried by the instruction, and sending a response message carrying license information to the service terminal device;

by the data-invoking-service sub-processor, according to the patient information carried by the instruction, retrieving the mapped service serial number;

by the data-invoking-service sub-processor, according to the service serial number, retrieving and invoking data that meet the instruction parameters;

by the data-invoking-service sub-processor, providing the invoked data to the service terminal device for browsing, reading, real-time live broadcast, and historical playback; and by the data-invoking-service sub-processor, saving a record of the data-invoking-service operation into a business-information database.

14. The method according to claim 12, wherein the third-party-business service further comprises a medical-document service, and a process of the medical-document service comprises the steps of:

by the service terminal device, inputting patient information and information of type of a medical document, and sending a medical-document service instruction to the cloud platform;

by the data communicator, sending the received instruction to a medical-document managing sub-processor;

by the medical-document managing sub-processor, receiving the instruction, resolving the instruction, authenticating user information and a validity state of user privilege that are carried by the instruction, and sending a response message carrying license information to the service terminal device;

by the medical-document managing sub-processor, according to the patient information carried by the instruction, retrieving the mapped service serial number;

when the service serial number has been retrieved, by the medical-document managing sub-processor, according to the service serial number and the information of the type of the medical document, retrieving and selecting a medical-document file that meets the instruction parameters; and by the service terminal device, performing creating, editing, inquiring, and maintaining of the selected medical-document file by handwriting, voice or spelling, and saving the medical-document file that has been processed into the file database;

when the retrieving result of the service serial number is void, by the medical-document managing sub-processor, according to the patient information, creating a medical document that meets the instruction parameters, editing the medical document, and saving the medical-document file that has been processed into the file database; and by the medical-document managing sub-processor, saving a record of the medical-document managing operation into a business-information database.

15. The method according to claim 12, wherein the third-party-business service further comprises a user-self-defined-term setting service, and a process of the user-self-defined-term setting service comprises the steps of:

by the service terminal device, selecting a user-self-defined term, inputting a setting content, and sending a user-self-defined-term setting instruction to the cloud platform;

by the data communicator, sending the received instruction to a user-self-defined-term setting sub-processor;

by the user-self-defined-term setting sub-processor, receiving the instruction, resolving the instruction, authenticating user information and a validity state of user privilege that are carried by the instruction, and sending a response message carrying license information to the service terminal device;

by the service terminal device, performing setting operations of editing, updating and storing of the user-self-defined term, and by the cloud platform, executing the setting as updated; and by the user-self-defined-term setting sub-processor, saving a record of the setting operation into a business-information database.

16. The method according to claim 12, wherein the third-party-business service further comprises a device-remote-operation service, and a process of the device-remote-operation service comprises the steps of:

by the service terminal device, inputting information of one or more patients and information of type of a remote operation, and sending a device-remote-operation instruction to the cloud platform;

by the data communicator, sending the received instruction to a device-remote-operation sub-processor;

by the device-remote-operation sub-processor, receiving the instruction, resolving the instruction, authenticating user information and a validity state of user privilege that are carried by the instruction, and sending a response message carrying license information to the service terminal device;

by the device-remote-operation sub-processor, according to IDs of one or more vital-sign monitoring devices mapped by the patient information, retrieving devices that meet the instruction parameters, and establishing a connection;

by the service terminal device, performing operations of control measurement, state inquiring, configuration modification and equipment maintenance of the connected vital-sign monitoring devices;

by the service terminal device, completing the connection and operation, and by the device-remote-operation sub-processor, saving the acquired operation result into a corresponding database according to the data type; and by the device-remote-operation sub-processor, saving a record of the device remote operation into a business-information database.

* * * * *